(12) United States Patent
Morimoto

(10) Patent No.: US 10,845,604 B2
(45) Date of Patent: Nov. 24, 2020

(54) MOUNTING APPARATUS FOR HEAD-MOUNTED DISPLAY

(71) Applicant: Sony Corporation, Tokyo (JP)

(72) Inventor: Toshiyasu Morimoto, Kanagawa (JP)

(73) Assignee: Sony Corporation, Tokyo (JP)

( * ) Notice: Subject to any disclaimer, the term of this patent is extended or adjusted under 35 U.S.C. 154(b) by 197 days.

(21) Appl. No.: 14/429,371

(22) PCT Filed: Sep. 12, 2013

(86) PCT No.: PCT/JP2013/005405
§ 371 (c)(1),
(2) Date: Mar. 19, 2015

(87) PCT Pub. No.: WO2014/050001
PCT Pub. Date: Apr. 3, 2014

(65) Prior Publication Data
US 2015/0219901 A1    Aug. 6, 2015

(30) Foreign Application Priority Data

Sep. 26, 2012  (JP) .................................. 2012-212087

(51) Int. Cl.
  *G09G 5/00*    (2006.01)
  *G02B 27/01*   (2006.01)
  (Continued)

(52) U.S. Cl.
  CPC ....... *G02B 27/0176* (2013.01); *G02B 27/017* (2013.01); *H04N 7/183* (2013.01); *A61B 1/00048* (2013.01)

(58) Field of Classification Search
  None
  See application file for complete search history.

(56) References Cited

U.S. PATENT DOCUMENTS 1,356,708 A  * 10/1920  Goodyear ............... G02B 7/002
                                                          351/156
2,769,176 A  * 11/1956  Grancsay ............... A42B 3/085
                                                          2/421

(Continued)

FOREIGN PATENT DOCUMENTS

CN          1600035 A      3/2005
CN          1934485 A      3/2007
(Continued)

OTHER PUBLICATIONS

Ohtsuki et al., Analysis on Characteristics of a C-Shaped Constant-Force Spring with a Guide, JSME International Journal, Series C, vol. 44, No. 2, 2001, p. 494-499.*

(Continued)

*Primary Examiner* — Lunyi Lao
*Assistant Examiner* — Kirk W Hermann
(74) *Attorney, Agent, or Firm* — Wolf, Greenfield & Sacks, P.C.

(57) ABSTRACT

There is provided a mounting apparatus for dispersing a weight of a device, the mounting apparatus comprising a main body configured to support the device and configured to mount on a head of a user and a support mechanism, connected to the device and the main body, comprising an elastic member configured to have a first length when the mounting apparatus is not mounted on the head of the user such that a first biasing force is applied; and have a second length larger than the first length when the mounting apparatus is mounted on the head of the user such that the weight of the device is dispersed by applying a second biasing force, which is greater than the first biasing force, with a force component in the vertical direction to the device.

22 Claims, 14 Drawing Sheets

(51) Int. Cl.
*H04N 7/18* (2006.01)
*A61B 1/00* (2006.01)

(56) References Cited

U.S. PATENT DOCUMENTS

| | | | | |
|---|---|---|---|---|
| 4,651,201 | A * | 3/1987 | Schoolman | A61B 1/00048 348/45 |
| 4,703,879 | A * | 11/1987 | Kastendieck | A42B 3/04 2/422 |
| 4,766,610 | A * | 8/1988 | Mattes | A42B 3/127 2/414 |
| 4,775,217 | A | 10/1988 | Ellis | |
| 5,005,213 | A * | 4/1991 | Hanson | F41G 3/165 224/181 |
| 5,412,811 | A * | 5/1995 | Hildenbrand | A42B 3/0433 2/10 |
| 5,572,749 | A * | 11/1996 | Ogden | A42B 3/14 2/410 |
| 5,949,388 | A * | 9/1999 | Atsumi | G02B 27/0172 345/53 |
| 5,954,642 | A * | 9/1999 | Johnson | G02B 27/017 600/300 |
| 5,959,780 | A * | 9/1999 | Togino | G02B 27/0172 359/630 |
| 6,012,164 | A * | 1/2000 | Deal, III | A63B 71/10 2/9 |
| 6,201,646 | B1 | 3/2001 | Togino et al. | |
| 6,369,952 | B1 * | 4/2002 | Rallison | G02B 27/017 359/630 |
| 2002/0008677 | A1 | 1/2002 | Saito | G02B 27/0176 345/8 |
| 2003/0115661 | A1 * | 6/2003 | Dobbie | A42B 1/046 2/422 |
| 2007/0013611 | A1 * | 1/2007 | Nakabayashi | G02B 7/002 345/8 |
| 2009/0128450 | A1 * | 5/2009 | Nakabayashi | G02B 27/0176 345/8 |
| 2010/0007581 | A1 * | 1/2010 | Kato | G02B 27/0176 345/8 |
| 2013/0336631 | A1 * | 12/2013 | Kura | G02B 27/0172 386/230 |

FOREIGN PATENT DOCUMENTS

| | | |
|---|---|---|
| CN | 101726857 A | 6/2010 |
| EP | 0077193 A2 | 4/1983 |
| EP | 0077193 A3 | 10/1983 |
| JP | 05-130532 A | 5/1993 |
| JP | 06-315124 A | 11/1994 |
| JP | 08-079658 A | 3/1996 |
| JP | 08-313828 A | 11/1996 |
| JP | 09-023396 A | 1/1997 |
| JP | 10-221637 A | 8/1998 |
| JP | 11-187331 A | 7/1999 |
| JP | 11-298826 A | 10/1999 |
| JP | 2001-104331 A | 4/2001 |
| JP | 2002-247482 A | 8/2002 |
| JP | 2007-528743 A | 10/2007 |
| JP | 2011-514831 A | 5/2011 |
| JP | 2011-120790 A | 6/2011 |
| JP | 2011-145488 A | 7/2011 |
| WO | WO 0055672 A1 * | 9/2000 ......... G02B 27/0176 |

OTHER PUBLICATIONS

Ohtsuki et al., Analysis of Characteristics of a C-Shaped Constant-Force Spring With a Guide, 2001, JSME International Journal, Series C, vol. 44, No. 2, p. 494-499 (Year: 2001).*
Definition of arch, 2019, Merriam-Webster, https://www.merriam-webster.com/dictionary/arch, p. 1 (Year: 2019) (Year: 2019).*
Korean office action and English translation thereof for Application No. KR 10-2015-7006668 dated Jun. 20, 2019.
International Search Report and Written Opinion dated Apr. 24, 2014 in connection with International Application No. PCT/JP2013/005405.
International Preliminary Report on Patentability dated Apr. 9, 2015 in connection with International Application No. PCT/JP2013/005405.
European Communication Pursuant to Article 94(3) EPC dated Oct. 15, 2018 in connection with European Application No. 13 773 868.8.
Chinese Office Action dated Sep. 5, 2016 in connection with Chinese Application No. 201380048877.1 and English translation thereof.

* cited by examiner

[Fig. 4]

MOUNTING APPARATUS FOR HEAD-MOUNTED DISPLAY

CROSS-REFERENCE TO RELATED APPLICATIONS

This application is a National Stage of International Application No. PCT/JP2013/005405, filed in the Japanese Patent Office as a Receiving office on Sep. 12, 2013, which claims priority to Japanese Patent Application Number 2012-212087, filed in the Japanese Patent Office on Sep. 26, 2012, each of which is hereby incorporated by reference in its entirety.

TECHNICAL FIELD

The present disclosure relates to a head-mounted display that can be used for the medical purposes.

BACKGROUND ART

A head-mounted display (HMD) that a user puts on the head for, for example, viewing images is known. For example, as one of the HMDs, there is known an HMD including image display surfaces and display elements for right and left eyes (see, PTL 1). The HMD having such a configuration can display images having a parallax to the left and right eyes of the user through the left and right display surfaces, and hence can present three-dimensional (3D) images without crosstalk.

Meanwhile, also in an endoscope apparatus and the like used for medical purposes, a practical use of a 3D endoscope apparatus that can present 3D images is in consideration. An endoscopic surgery is less invasive for a patient than a general surgical operation, and hence is popular in recent years. However, an affected part(s) is checked only by images during a surgery, and hence it is sometimes difficult to perceive a depth with traditional two-dimensional (2D) images. Therefore, it is expected that connecting and using the HMD capable of providing 3D images to a 3D endoscope apparatus can realize a more correct and rapid endoscopic surgery while viewing realistic images of the affected part.

During an endoscopic surgery, when the mounting position of the HMD changes, it is difficult to correct the mounting position because the user's (doctor's) hands are sterilized. Thus, it is necessary to mount the HMD on the user such that the mounting position of the HMD with respect to the user does not change. For example, PTL 2 describes an HMD including a front pressing part that biases the forehead of the user and a rear pressing part that biases the occipital region.

CITATION LIST

Patent Literature

PTL 1: Japanese Patent Application Laid-open No. 2011-145488
PTL 2: Japanese Patent Application Laid-open No. HEI 11-298826

SUMMARY

Technical Problem

However, in the configuration in which the HMD is retained on the head by biasing the user, if the user wears the HMD for a long time as in the endoscopic surgery, the biasing force is continuously applied to the user. Therefore, in some cases, the user feels pain or uncomfortable.

In view of the above-mentioned circumstances, it is desirable to provide an HMD with less burden on the user during mounting.

Solution to Problem

According to an embodiment of the present technology, there is provided a mounting apparatus for dispersing a weight of a device, the mounting apparatus comprising a main body configured to support the device and configured to mount on a head of a user and a support mechanism, connected to the device and the main body, comprising an elastic member configured to have a first length when the mounting apparatus is not mounted on the head of the user such that a first biasing force is applied; and have a second length larger than the first length when the mounting apparatus is mounted on the head of the user such that the weight of the device is dispersed by applying a second biasing force, which is greater than the first biasing force, with a force component in the vertical direction to the device.

Advantageous Effects of Invention

As mentioned above, according to the embodiment of the present technology, it is possible to provide an HMD with less burden on the user.

DESCRIPTION OF EMBODIMENTS

Hereinafter, embodiments according to the present technology will be described with reference to the drawings.

First Embodiment

Endoscopic System

Figure 1:
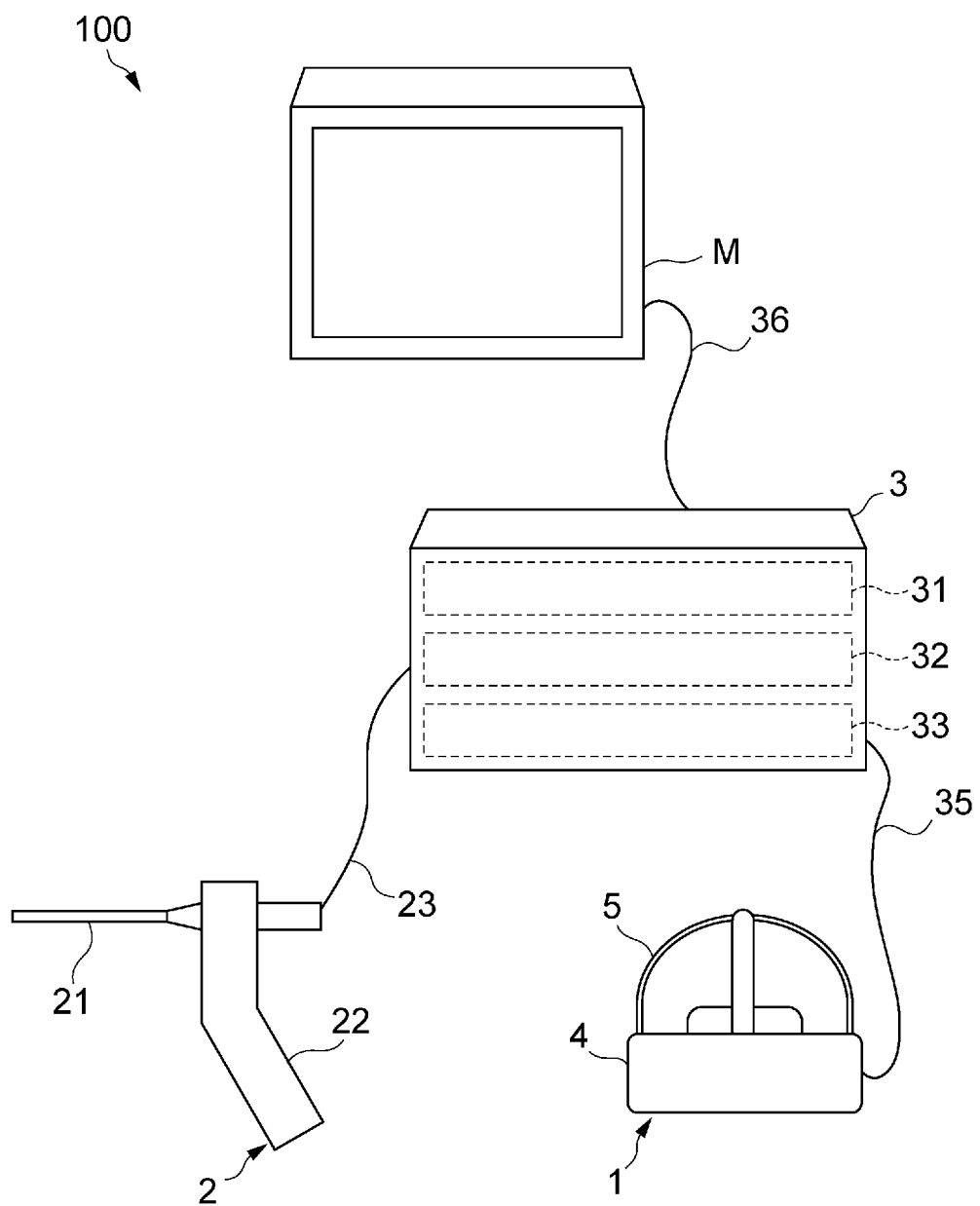
FIG. 1 is a view schematically showing a configuration example of an endoscopic system according to a first embodiment of the present technology.

FIG. 1 is a view schematically showing a configuration example of an endoscopic system according to an embodiment of the present technology. An endoscopic system 100 according to this embodiment includes a head-mounted display (HMD) 1, an endoscope apparatus 2, and a processor unit 3. The endoscopic system 100 according to this embodiment is used in the following manner. Specifically, during an endoscopic surgery, a doctor (user) wearing the HMD 1 inserts the endoscope apparatus 2 into the body of a patient and performs treatments such as resection on an affected part(s) while checking, through the HMD 1, a state of the affected part that is imaged by the endoscope apparatus 2.

The endoscope apparatus 2 includes, for example, an insertion portion 21 and an operation portion 22. The insertion portion 21 has a tubular shape that can be inserted into a body. The insertion portion 21 includes therein an image sensor such as a CMOS (complementary metal-oxide semiconductor) image sensor and an optical system such as a lens for imaging an affected part(s), which are not shown in the figure. Further, in this embodiment, two image sensors, two optical systems, and the like are provided for capturing right-eye and left-eye images having a parallax. With this, 3D image data for stereoscopically displaying the affected part can be acquired.

The operation portion 22 is configured to perform an operation on the insertion portion 21 and the like while gripped by a surgery assistant or the like. Further, the operation portion 22 is connected to the processor unit 3 via a cable 23.

The processor unit 3 includes, for example, an image processing unit 31, a light source 32, and a converter 33. For example, the image processing unit 31 serves to process images acquired by the endoscope apparatus 2. The light source 32 serves to irradiate the affected part with light upon imaging by the endoscope apparatus 2. The converter 33 serves to perform conversion processing on signals relating to images to be outputted to the HMD 1. The light emitted from the light source is guided to a distal end of the insertion portion 21 via, for example, light guide fibers provided inside the insertion portion 21.

Further, in the image processing unit 31, the right-eye and left-eye images captured can be overlapped and processed as the 3D image data. The 3D image data is outputted to a monitor apparatus M via, for example, a cable 36, which allows a helper and the like other than the user wearing the HMD 1 to also check the affected part during the surgery.

The HMD 1 is electrically connected to the processor unit 3 and worn by the user who makes instructions to the surgery assistant or the like who operates the endoscope apparatus 2 while the user is observing endoscopic images. The connection method for the HMD 1 and the processor unit 3 is not particularly limited and a wired connection or a wireless connection may be used. In this embodiment, for example, the wired connection is used. Specifically, the HMD 1 and the processor unit 3 are connected to each other via a cable 35 outputted and inputted from/to display port terminals.

The signals relating to the right-eye and left-eye images captured by the endoscope apparatus 2 are processed as image signals by the image processing unit 31. After that, the image signals are each processed by the converter 33 as image data adapted for the HMD 1, and outputted to the HMD 1 via the cable 35. Note that, the processor unit 3 may be configured to supply the HMD 1 with a driving electrical power via the cable 35.

Note that, the converter 33 that processes output signals to the HMD 1 is not limited to the example shown in the figure in which the converter 33 is housed in a single casing together with the image processing unit 31 and the like. The converter 33 may be housed in a separate casing other than that for the image processing unit 31 and the like.

Next, a detailed configuration of the HMD 1 according to this embodiment will be described.

HMD

Figure 2:
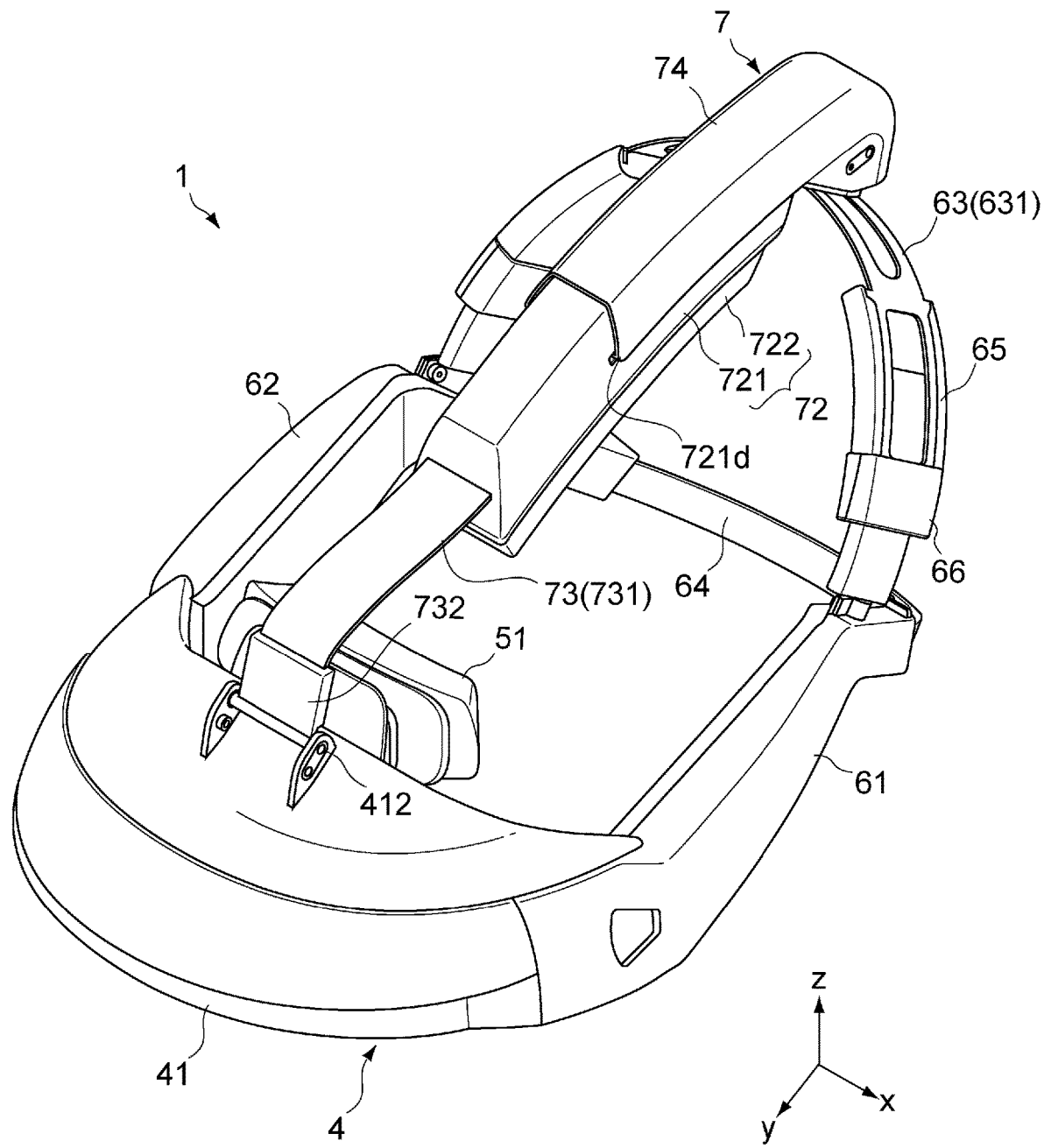
FIG. 2 is a perspective view showing a configuration of a head-mounted display (HMD) according to the first embodiment of the present technology.
Figure 3:
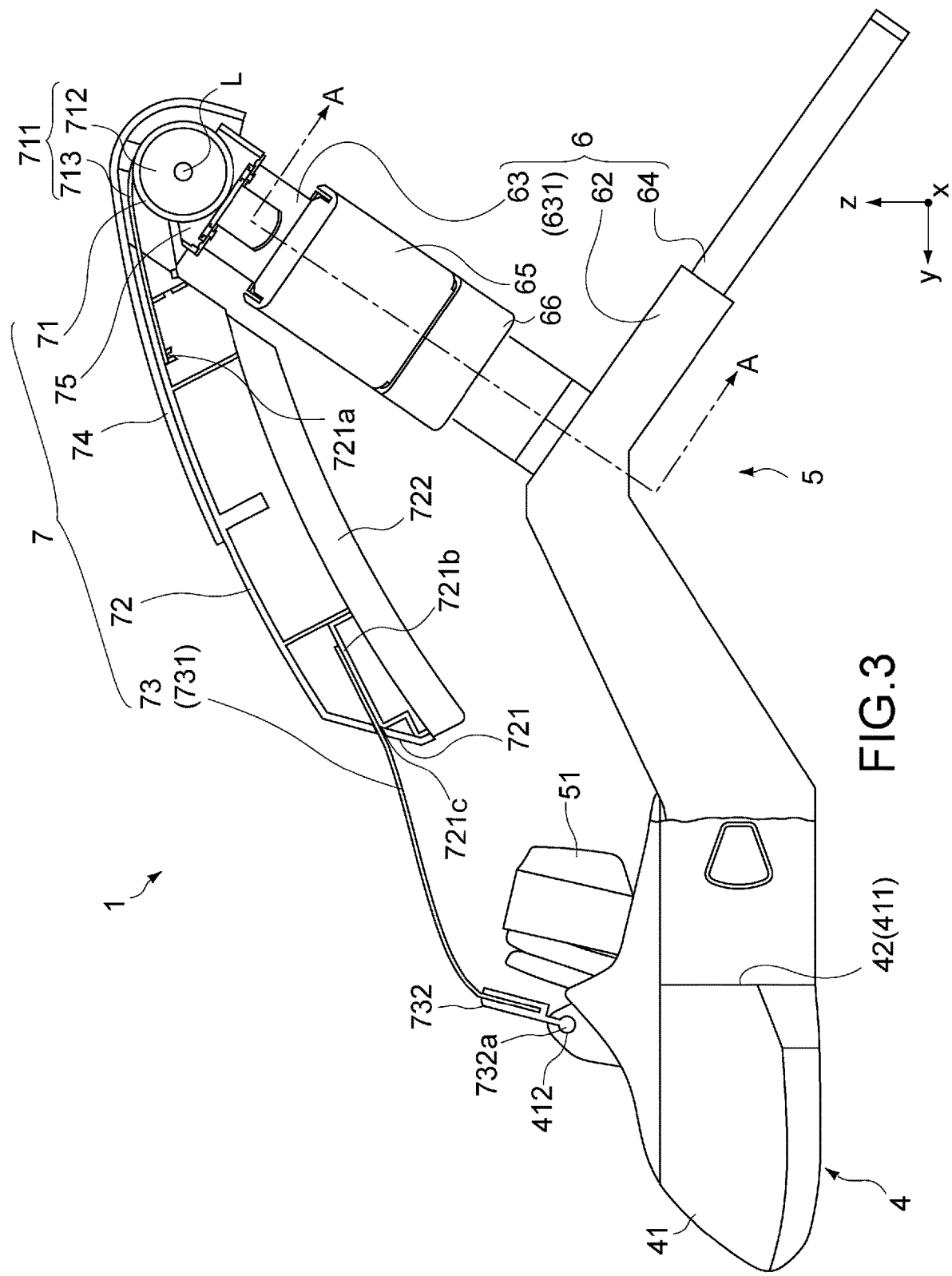
FIG. 3 is a cross-sectional view of the HMD shown in FIG. 2 as viewed in an x-axis direction.
Figure 4:
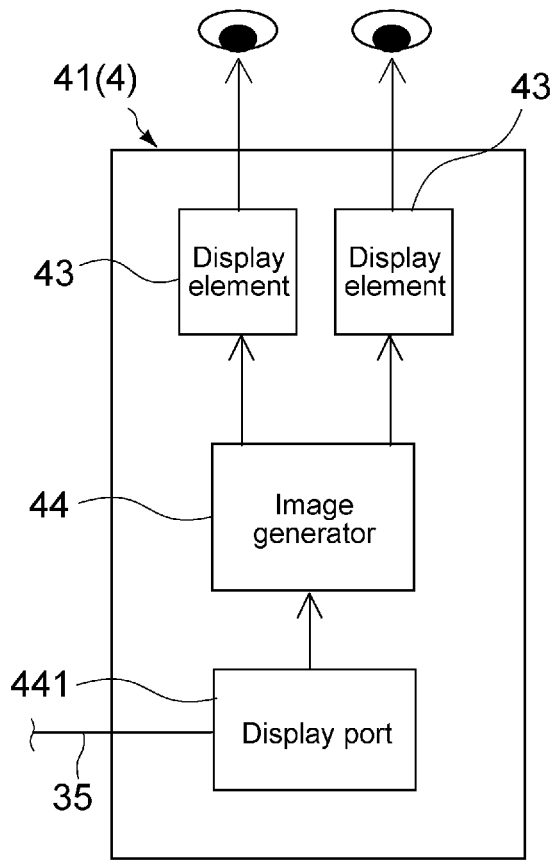
FIG. 4 is a block diagram showing an inner configuration of the HMD (display unit) shown in FIG. 2.

FIGS. 2 to 4 are views each showing a configuration of the HMD 1 according to this embodiment. FIG. 2 is a perspective view. FIG. 3 is a cross-sectional view as viewed in the x-axis direction. FIG. 4 is a block diagram showing an inner configuration. The HMD 1 includes a display unit 4 and a mounting unit 5. The mounting unit 5 includes a support mechanism 7.

Note that, an x-axis direction and a y-axis direction in the figures each indicate a horizontal direction in an xyz coordinate system to which the HMD 1 belongs. The x-axis direction is a "second axis direction" and corresponds to left and right directions of the HMD 1. The y-axis direction is a "first axis direction" and corresponds to front and rear directions of the HMD 1, which are orthogonal to the x-axis direction. A z-axis direction indicates a direction orthogonal to the x-axis direction and the y-axis direction and corresponds to upper and lower directions of the HMD 1. Note that, also in the state in which the HMD 1 is worn by the user, the x-axis direction is set to be left- and right-hand directions of the user, the y-axis direction is set to be front and rear directions of the user, and the z-axis direction is set to be upper and lower directions of the user.

The HMD 1 according to this embodiment is formed of, for example, a goggle-shaped non-see-through HMD. Further, the display unit 4 is provided with the mounting portion 5, which will be described later. When the mounting portion 5 is mounted on the head of the user, the display unit 4 is located in front of the left and right eyes of the user.

Hereinafter, configurations of the respective components will be described.

Display Unit

The display unit 4 includes a casing 41, display surfaces (display surface) 42 for the left and right eyes, display elements 43 for the left and right eyes, and an image generator 44. Note that the display surfaces (display surface) 42 and the display elements 43 have the same configuration for both the left and right eyes, and hence will be denoted by the same reference symbols and described.

The display unit 4 is configured as an image display apparatus that presents a predetermined image captured by the endoscope apparatus 2 to the user. Specifically, the image generator 44 first generates, based on image data acquired via the processor unit 3, image signals to be outputted to the left and right display elements 43, respectively. Then, the display elements 43 emit image light beams corresponding to those image signals to the display surfaces 42, respectively, so that images are presented to the user.

The casing 41 is, as a whole, configured to fit the face, covering the left and right eyes of the user. The casing 41 is, as a whole, formed in a semi-disk-shape bulging in the y-axis direction. The casing 41 is configured to cover the eyes of the user.

Further, the casing 41 includes an eye-side surface 411. The eye-side surface 411 is opposed to the left and right eyes of the user and is almost orthogonal to the y-axis direction. The eye-side surface 411 is configured to be opposed to the left and right eyes of the user in front of and in proximity to the left and right eyes. For example, in the center of the eye-side surface 411, a cutout may be formed corresponding to the nose shape of the user.

A pad portion 51 (to be described later) is provided on an upper surface of the casing 41. The pad portion 51 is brought into contact with the forehead of the user upon mounting to fix a mounting position of the display unit 4. Further, a pair of protrusions are arranged in the upper surface of the casing 41. The pair of protrusions respectively have attachment holes 412. The pair of attachment holes 412 are opposed to each other in the x-axis direction. An auxiliary member 73 of the support mechanism 7 to be described later are attached into the pair of attachment holes 412.

The left and right side surfaces of the casing 41 are continuous with left and right connection members 61 and 62 of the mounting unit 5, each of which will be described later.

Upon mounting, the thus configured casing 41 can almost completely cover the eyes of the user. Thus, light from the outside is not incident upon the eyes of the user, which makes it easier for the user to view images.

The casing 41 houses the display elements 43, the image generator 44, and the like. Note that the shape of the casing 41 is not limited to the above-mentioned semi-disk-shape as long as the casing 41 can house those elements and cover the eyes of the user. For example, the shape of the casing 41 may be a rectangular parallelepiped shape.

In the eye-side surface 411, the display surfaces 42 are arranged along the x-axis direction. The display surfaces 42 are arranged to be orthogonal to the y-axis direction so that optical axe of the outputted image light beams are parallel to the y-axis direction.

The display surfaces 42 are configured to be capable of displaying the right-eye and left-eye images, which have been captured by the endoscope apparatus 2 and subjected to predetermined processing, to the left eye and the right eye of the user, respectively. The shape and size of the display surfaces 42 are not particularly limited. In this embodiment, each of the display surfaces 42 has a rectangular shape with about 16 mm in the vertical direction and about 30 mm in the horizontal direction. The material of the display surfaces 42 is not particularly limited as long as it has a see-through property. For example, a plastic plate, a glass plate, or the like is used as the material of the display surfaces 42.

In this embodiment, the image generator 44 includes an image data conversion circuit or the like that converts the right-eye and left-eye image data sent from the processor unit 3 into the image signals for the HMD 1. The image generator 44 acquires endoscopic image data from a display port input terminal 441 connected to the cable 35.

In addition, the image generator 44 may perform predetermined offset processing or the like on the image data to generate left-eye and right-eye image signals suitable for the HMD 1. With this, it is possible to present a desired 3D image to the user. The amount of offset in the offset processing is calculated based on, for example, distances between eyes and the display elements 43 of the HMD 1, a distance between both eyes, or a virtual image position, which will be described later.

The image generator 44 outputs the generated left-eye and right-eye image data to the left and right display elements 43, respectively.

The left and right display elements 43 output, based on the image data inputted from the image generator 44, the image light beams to the left and right display surfaces 42. The display elements 43 are arranged to be respectively opposed to the display surfaces 42 in the y-axis direction, for example. With this, the optical axes of the image light beams, which are outputted from the display elements 43 and the display surfaces 42, become parallel to the y-axis direction.

In this embodiment, the display elements 43 are formed of organic electroluminescence (EL) elements. The use of the organic EL elements as the display elements 43 can achieve downsizing, high contrast, a rapid response, and the like.

As the display elements 43, for example, a plurality of red organic EL elements, green organic EL elements, blue organic EL elements, and the like are arranged in a matrix form. By being driven by a driving circuit of active matrix type, simple (passive) matrix type, or the like, these elements emit light by themselves at a predetermined timing with a predetermined luminance and the like. Further, the display elements 43 are configured to display a predetermined image as a whole by the driving circuit being controlled according to the image signals generated by the image generator 44.

Note that, the display elements 43 are not limited to the above-mentioned configuration. For example, a liquid crystal display (LCD) and the like may be used.

Between the display elements 43 and the display surfaces 42, for example, a plurality of eye lenses (not shown) are provided as optical systems. By causing these eye lenses and the eyes of the user to be opposed to each other with a predetermined distance therebetween, it is possible for the user to observe a virtual image as if the virtual image is displayed at a predetermined position (virtual image position). The virtual image position and the size of the virtual image are set depending on the configurations of the display elements 43 and the optical systems and the like. For example, the size of the virtual image is 750 inches adapted for a movie size and the virtual image position is set to be located at a position away from the user by about 20 m.

Here, in order to allow the user to observe the virtual image, the display unit 4 is positioned with respect to the user so that the image light beams outputted from the display elements 43, with the y-axis direction being an optical axis direction thereof, form images respectively on the irises of the left and right eyes through the eye lenses and the like.

Therefore, in order to allow the user to observe the predetermined image, it is necessary to position the display unit 4 so that the display surfaces 42 and the left and right eyes of the user are opposed to each other in the y-axis direction. In other words, the display unit 4 is positioned at a relative position suitable for the user so that the x-axis direction in which the display surfaces 42 are arranged becomes parallel to a line linking between the left and right eyes of the user.

When the display unit 4 is not located at the suitable relative position, an out-of-focus image or a blurred 3D image is generated and the user cannot view a desired image. Further, during an endoscopic surgery, it is difficult for the user to correct the mounting position of the HMD 1 for a long time because the user's hands are sterilized. With this, upon the mounting of the HMD 1 before a surgery, it is necessary to adjust the display unit 4 to be located at the suitable relative position. Further, during the mounting, it is necessary to fix the display unit 4 to the head such that this position does not change.

Further, the display unit 4 according to this embodiment includes a plurality of eye-side lenses as an optical system, and has a weight of about 400 g, for example. Thus, in order to retain the display unit 4 at a suitable relative position with respect to the head of the user, it is necessary to support the display unit 4 such that the display unit 4 does not fall due to its weight. In this case, a mounting method in which the mounting member is tightened with respect to the user with a large force and the display unit 4 is retained due to a counteracting force thereof is generally used. However, such a mounting method places a large burden on the user. In some cases, the user feels pain or uncomfortable.

In view of this, the HMD 1 according to this embodiment includes the mounting unit 5 to be described in the following. Thus, it is possible to retain the mounting position of the display unit 4 and reduce the burden on the user during mounting.

Mounting Unit

The mounting unit 5 includes a main body 6 and the support mechanism 7. The main body 6 supports the display unit 4 and is mounted on the head of the user. The support mechanism 7 is connected between the display unit 4 and the main body 6 to be capable of generating a biasing force to contribute as a tensile force with respect to the display unit during mounting. Hereinafter, a specific configuration will be described.

The main body 6 includes three members mounted on the head of the user. Specifically, the main body 6 includes the two (left and right) connection members 61 and 62, a coupling member 63, and a band member 64. The two (left and right) connection members 61 and 62 are connected to the display unit 4 and opposed to each other in the x-axis direction (left- and right-hand directions). The coupling member 63 couples between the connection members 61 and 62 in an arch form. The band member 64 is connected between the connection members 61 and 62 and opposed to the display unit 4 in the y-axis direction.

The connection members 61 and 62 are, at one ends, continuous with the left and right side surfaces of the casing 41 of the display unit 4 and are, at the other ends, continuous with the band member 64. For example, the connection members 61 and 62 are configured to extend almost in parallel to the y-axis direction as viewed in the z-axis direction and to be partially bent upwards in the z-axis direction as viewed in the x-axis direction. With this, the connection members 61 and 62 are arranged to pass through above the auricles from the left and right temporal regions when attached to the user, reach the back of the auricles, and be connected to the band member 64.

The connection members 61 and 62 may be configured to be capable of bowing with respect to the display unit 4 in the left- and right-hand directions. Examples of the material of such connection members 61 and 62 include a nylon resin and a polypropylene resin. Further, for example, soft materials such as sponge made of urethane foam may be bonded to sides of the connection members 61 and 62 to be brought into contact with the user. With this, it is possible to improve a wearing comfort of the user. In addition, by covering those materials with a synthetic leather or the like, it is possible to prevent contamination by blood and the like that scatter during a surgery and to improve the wearing comfort.

The coupling member 63 is formed in an arch shape as a whole. The coupling member 63 is, at both end portions, connected to the connection members 61 and 62, and is, at a top (center) portion, connected to the support mechanism 7. In other words, the coupling member 63 has a structure including a left arm attached to the left temporal region and a right arm attached to the right temporal region with the center portion connected to the support mechanism 7 being a boundary.

Connection positions between the both end portions of the coupling member 63 and the connection members 61 and 62 are not particularly limited. However, for example, if the connection positions are located in portions of the connection members 61 and 62 that are bent in the z-axis direction, it is possible to shorten the coupling member 63. Further, a connection method between the coupling member 63 and the connection members 61 and 62 is not also particularly limited. For example, the coupling member 63 and the connection members 61 and 62 may be fixed to each other with screws or the like via separate members for connection. Alternatively, the end portions of the coupling member 63 may be inserted and fitted into the connection members 61 and 62.

In this embodiment, the coupling member 63 includes a base material 631 and left and right length adjustment mechanisms 65. The base material 631 has a top portion connected to an elastic member 71 and is formed to be curved. The left and right length adjustment mechanisms 65 are respectively connected to the left and right end portions of the base material 631, and respectively connected to the connection members 61 and 62. Note that the left and right length adjustment mechanisms 65 both have the same configuration, and will be denoted by the same reference symbols and described.

The base material 631 is configured to be curved at a curvature lower than a curvature of the head of an average user. For example, the base material 631 is formed of an elastic metal or the like such as stainless steel (SUS). Such a base material 631 enables the coupling member 63 to be fitted onto the head of the user upon mounting. Further, a connection method for the base material 631 and the length adjustment mechanisms 65 is not particularly limited. For example, a base-material attachment member 66 may be attached to around a housing 651 of each of the length adjustment mechanisms 65 to be described later. The base material 631 may be inserted into between the base-material attachment member 66 and the housing 651, and fixed with screws or the like.

Each of the length adjustment mechanisms 65 is configured to be capable of adjusting the length of the coupling member 63 between the support mechanism 7 and each of the connection members 61 and 62. The length adjustment mechanisms 65 are connected to the base material 631 while sandwiching the support mechanism 7 therebetween, and attached to the left and right temporal regions upon mounting. That is, the length adjustment mechanisms 65 according to this embodiment include the end portions to be connected to the connection members 61 and 62, respectively, and form the left and right arms of the coupling member 63. Note that the left and right length adjustment mechanisms 65 both have the same configuration, and will be denoted by the same reference symbols and described.

Figure 5:
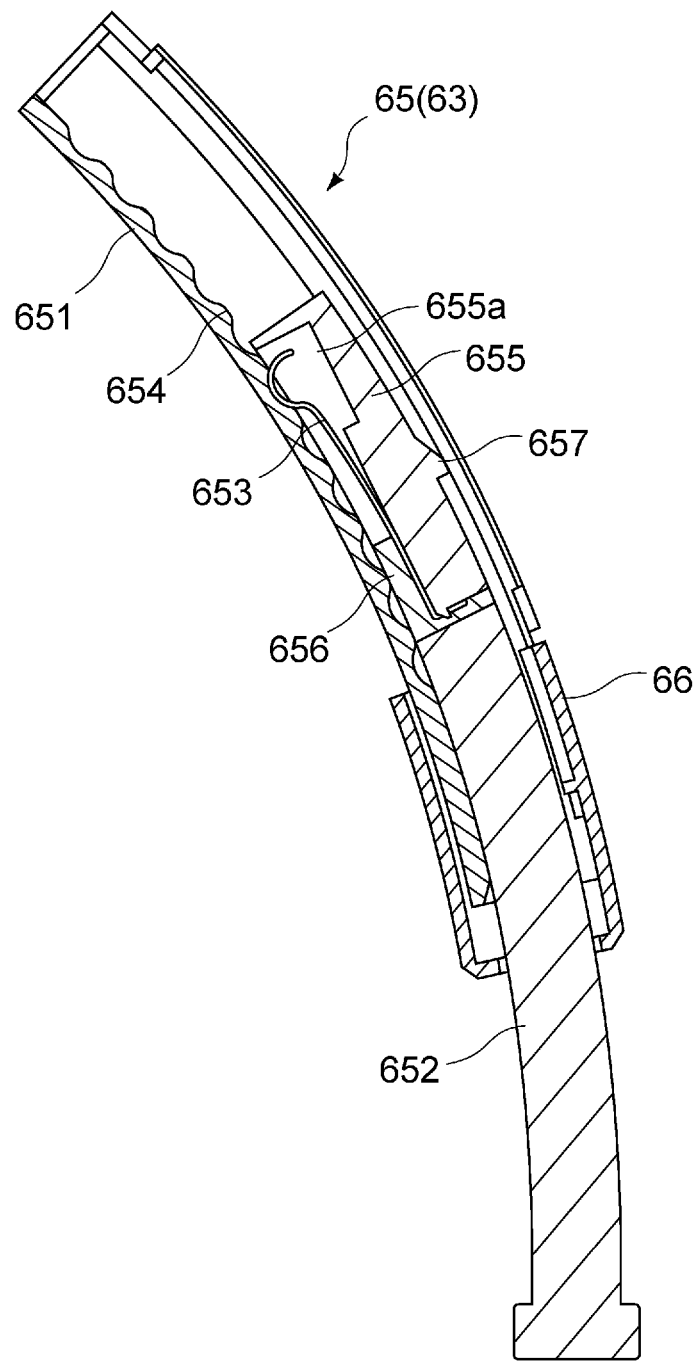
FIG. 5 is a view showing a configuration example of a length adjustment mechanism of the HMD shown in FIG. 2, more particularly, a cross-sectional view as viewed in the A-A direction of FIG. 3.

FIG. 5 is a cross-sectional view showing a configuration example of the length adjustment mechanisms 65, as viewed in the A-A direction of FIG. 3. The configurations of the length adjustment mechanisms 65 are not particularly limited. For example, as shown in FIG. 5, each of the length adjustment mechanisms 65 may include the housing 651, a slider member 652, and a spring material 653. The slider member 652 may be engaged to the housing 651 via the spring material 653 while the slider member 652 may be movable with respect to the housing 651. Note that, in FIG. 5, illustration of the base material 631 is omitted.

The housing 651 is connected to the base material 631, and formed in a sheath-like shape extending to be curved. The housing 651 may include an undulating structure 654 in an inner surface thereof. For example, the undulating structure 654 is a periodical smooth concavo-convex structure. For example, the undulating structure 654 is configured to correspond to the shape of an end of the spring material 653. Further, for example, the undulating structure 654 is formed in the inner surface of the housing 651 located on a side to be attached to the user.

The slider member 652 is connected to the connection member 61 (or connection member 62), and configured to be inserted into the housing 651 at one end thereof. In addition, the slider member 652 is configured to be movable with respect to the housing 651 in a longitudinal direction. Note that the slider member 652 includes a stopper 657 protruding to the housing 651, and hence the slider member 652 can be prevented from falling out of the housing 651 from the end portion thereof.

The spring material 653 is formed to be engageable to the undulating structure 654, and retained by the slider member 652. The shape of the spring material 653 is not particularly limited as long as the spring material 653 is engageable to the undulating structure 654. However, as shown in FIG. 5, the spring material 653 may be curved such that the end of the spring material 653 is engaged to a concave portion of the undulating structure 654. A metal or the like generally used as a plate spring is employed for the material of the spring material 653. Examples of the material of the spring material 653 include SUS and phosphor bronze.

The configuration retaining the spring material 653 in the slider member 652 is not particularly limited. For example, the slider member 652 may include a first retaining portion 655 and a second retaining portion 656. The first retaining portion 655 is held in contact with the undulating structure 654. A recess portion 655a is formed in the first retaining portion 655. The spring material 653 is placed in the recess portion 655a. The second retaining portion 656 is placed in a recess portion and sandwiches the spring material 653 with the first retaining portion 655. The spring material 653 is retained by the first retaining portion 655 and the second retaining portion 656. Thus, the spring material 653 can bow in a thickness direction of the housing 651. Here, the term of "the thickness direction of the housing 651" means a direction almost orthogonal to an inner surface in which the undulating structure 654 is formed.

In the above-mentioned configuration example, the length adjustment mechanisms 65 adjust the length of the coupling member 63 in the above-mentioned manner. First, a force having a predetermined magnitude or more is added to the slider member 652 in a longitudinal direction of the coupling member 63. Then, the spring material 653 bows in the thickness direction of the housing 651. The engagement between the spring material 653 and a concave portion of the undulating structure 654 is released. The slider member 652 moves in the longitudinal direction. As a result, the spring material 653 is engaged to a neighbor concave portion of the undulating structure 654. The length of the coupling member 63 changes by an amount corresponding to a concavo-convex cycle of the undulating structure 654. Thus, the length adjustment mechanisms 65 can change the length in a step-wise manner. At the same time, the elastic force of the spring material 653 can provide the user with a click feeling.

Meanwhile, in the case where a force pulling the slider member 652 is smaller than the predetermined force, an elastic force of the spring material 653 keeps the engagement state between the spring material 653 and the undulating structure 654. That is, upon normal mounting in which such a force is not generated in the longitudinal direction of the coupling member 63 that the engagement between the spring material 653 and the undulating structure is released, the length of the coupling member 63 is kept. The mounting state of the HMD 1 can be kept.

The band member 64 is, as a whole, formed in a single band-like shape, for example. The band member 64 is, at both end portions thereof, connected to the connection members 61 and 62. A connection method for the band member 64 and the connection members 61 and 62 is not particularly limited. For example, a method in which the end portions of the band member 64 are inserted into the connection members 61 and 62 through insertion holes or the like and the end portions adhere to insides of the connection members 61 and 62 can be employed.

The band member 64 is formed of, for example, a soft material. Specifically, a silicone rubber, a thermosetting resin-based elastomer such as a urethane rubber, cloth made of polypropylene or the like, a resin material such as polyvinyl chloride, a vulcanized rubber, or the like may be used. Such a band member 64 may be configured to be fit the shape of the occipital region of the user.

Further, the band member 64 may include a length adjustment mechanism as in the coupling member 63. The configuration of that mechanism is not particularly limited. However, for example, a configuration capable of adjusting the length in a step-wise manner similar to the length adjustment mechanisms 65 shown in FIG. 5 may be employed.

The thus configured main body 6 supports the display unit 4 and the support mechanism 7. The support mechanism 7 is connected to the display unit 4 and the coupling member 63. For example, the support mechanism 7 is attached to extend from the frontal region to a rear portion of the parietal region of the user. Hereinafter, a specific configuration of the support mechanism 7 will be described.

The support mechanism 7 includes the elastic member 71, a contact member 72, and the auxiliary member 73. In the support mechanism 7, the auxiliary member 73, the contact member 72, and the elastic member 71 are connected to one another in series in the stated order from a side of the display unit 4. The elastic member 71 is connected to the coupling member 63.

The elastic member 71 has a first length during non-mounting. The elastic member 71 has a second length larger than the first length during mounting. For example, the first length is a natural length of the elastic member 71 and the second length is a length to exert an elastic force. That is, the elastic member 71 exerts an elastic force as the biasing force with respect to the display unit 4 by extending beyond the second length.

In this embodiment, the elastic member 71 includes a spring 711. The spring 711 is a so-called constant load spring that generates a constant elastic force with the second length and a third length larger than the second length. For example, the second length may be a minimum length to exert a constant elastic force. That is, as long as the spring 711 has the second length or more, the spring 711 exerts approximately a constant elastic force irrespective of a stroke. For example, a "CONSTON (registered trademark)" manufactured by SUNCO SPRING Co., Ltd. may be employed as such a spring 711.

Figure 6:
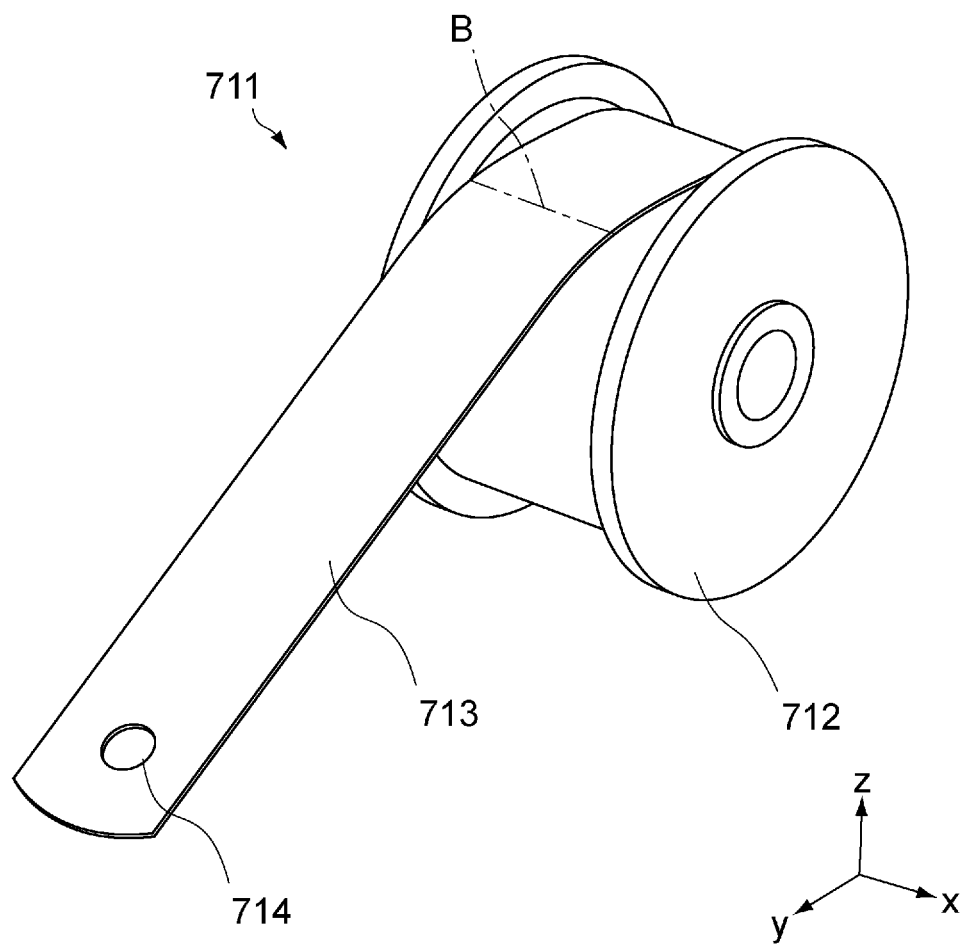
FIG. 6 is a perspective view showing a configuration of a spring of the HMD shown in FIG. 2.

FIG. 6 is a perspective view showing a configuration of the spring 711 according to this embodiment. The spring 711 includes a wheel 712 and a spring material 713. The wheel 712 is rotatable around an x-axis. The spring material 713 is wound around the wheel 712.

The wheel 712 is provided with a shaft hole into which a rotation shaft L is to be fitted. For example, the wheel 712 is made of a resin or a metal. The rotation shaft L is supported by a cover member 74 and a spring-supporting member 75 to be described later. In this embodiment, the rotation shaft L is provided parallel to the x-axis direction. Note that the illustration of the rotation shaft L is omitted in FIGS. 2 and 6.

The spring material 713 is typically made of a tape-like metal. For example, SUS is employed. The spring material 713 is provided with an attachment hole 714. The attachment hole 714 is formed at an end portion of the spring material 713 on a side on the spring material 713 is pulled out. The attachment hole 714 is fixed with a screw or the like to a first connection portion 721*a* (to be described later) of the contact member 72.

In the spring 711, by the contact member 72 moving with respect to the wheel 712 (rotation shaft L), the spring material 713 is pulled out from the wheel 712. The length of the spring 711 changes from the first length to the third length. In this embodiment, it is assumed that the "length" of the spring 711 means a length from a boundary B to the attachment hole 714 of the spring material 713, for example. Note that the boundary B is a virtual line on the spring material 713, which is a boundary between an area in which the spring material 713 pulled out from the wheel 712 is to be held in contact with the wheel 712 or the spring material 713 wound around the wheel 712 and an area in which the spring material 713 pulled out from the wheel 712 is to be spaced from the wheel 712 or the spring material 713 wound around the wheel 712.

The contact member 72 is connected to the display unit 4 and the elastic member 71. The contact member 72 is mounted on the head of the user such that the elastic member 71 has the second length upon mounting. Further, in this embodiment, the contact member 72 is connected to the display unit 4 via the auxiliary member 73. The contact member 72 includes a sheath member 721 and a spacer 722. The contact member 72 is configured to have a two-phase structure of the sheath member 721 and the spacer 722.

The sheath member 721 includes the first connection portion 721*a* and a second connection portion 721*b*. The first connection portion 721*a* is provided at an end portion on a side of the elastic member 71. The second connection portion 721*b* is provided at an end portion on a side of the auxiliary member 73. The sheath member 721 has an elongated structure formed along the head of the user as a whole. In this embodiment, a rear portion of the sheath member 721 being the end portion on the side of the elastic member 71 and a lower portion of the sheath member 721 being on the side of the user during mounting are opened. In addition, in the front surface being an end portion on the side of the display unit 4, an insertion hole 721*c* for inserting one end of the auxiliary member 73 into the inside is formed. A resin, a metal, or the like may be appropriately employed for the material of the sheath member 721.

The first connection portion 721*a* is connected to the elastic member 71. The first connection portion 721*a* is formed to inwardly protrude from an upper surface of the sheath member 721, for example. The first connection portion 721*a* is connected to the attachment hole 714 of the spring 711. For example, a method forming a screw hole in the first connection portion 721*a* and screwing between the attachment hole 714 of the spring 711 and the screw hole may be employed as a connection method. Further, the connection method is not limited thereto and an adhesive or the like may be connected.

The second connection portion 721*b* is connected to the auxiliary member 73. The second connection portion 721*b* may have a seat-like shape including an adhesive surface provided in an inside of the sheath member 721, for example. In this case, the second connection portion 721*b* is connected to the auxiliary member 73 in such a manner that one end of the auxiliary member 73 inserted through the insertion hole 721*c* adheres onto the adhesive surface. The method of connecting to the auxiliary member 73 is not limited thereto. For example, a method using a screw or the like as in the first connection portion 721*a* may be employed.

Figure 7:
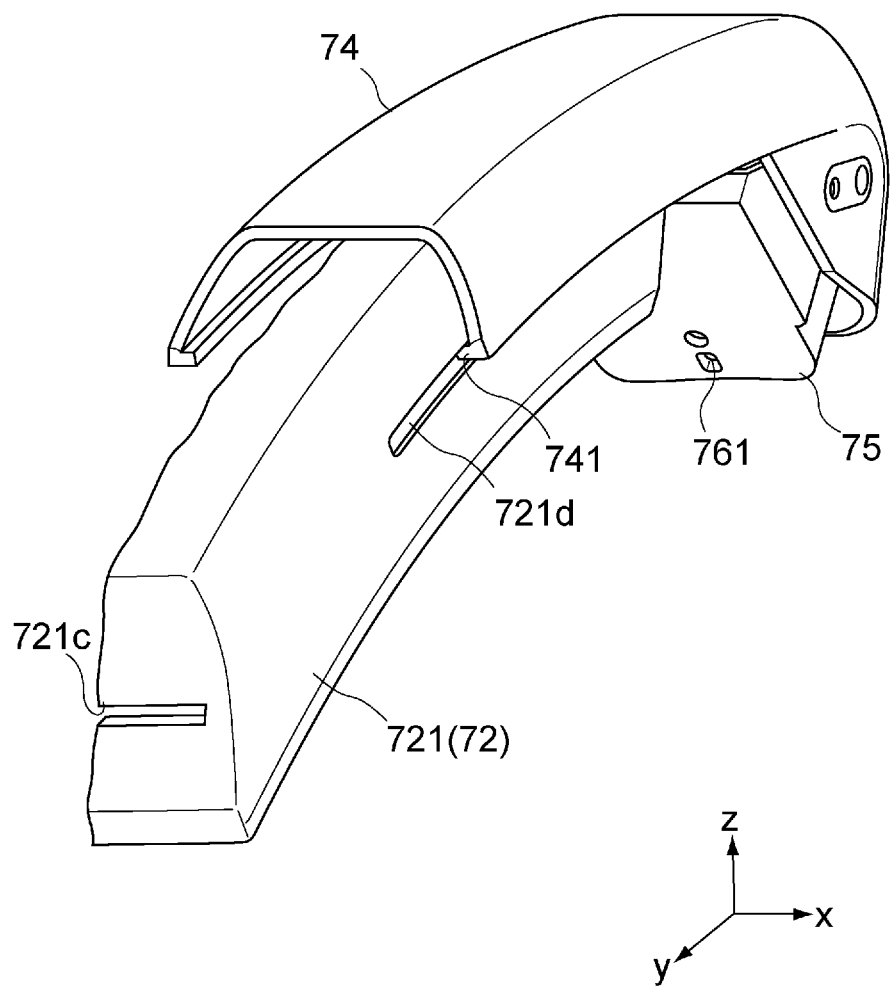
FIG. 7 is a perspective view showing configurations of main parts of a support mechanism of the HMD shown in FIG. 2.

In addition, the sheath member 721 includes a pair of engagement grooves 721*d* formed in the left and right side surfaces along the longitudinal direction (cf. FIGS. 2 and 7). The engagement grooves 721*d* are configured to be engaged to the cover member 74 to be described later while being slidable along the longitudinal direction of the sheath member 721. The configuration of the engagement grooves 721*d* is not particularly limited. For example, the engagement grooves 721*d* may be formed of holes passing from the side surfaces to the inside of the sheath member 721. Alternatively, the engagement grooves 721*d* may be recess portions formed in the left and right side surfaces.

The spacer 722 is formed along the longitudinal direction of the sheath member 721. The spacer 722 has a thickness in an almost perpendicular direction with respect to a top surface of the head. The spacer 722 is attached to a side of the sheath member 721 which is attached to the user, and held in contact with the user during mounting. The material of the spacer 722 is not particularly limited. For example, a material that generates a frictional force rearward in the y-axis direction when the material is held in contact with the head of the user and that has a high wearing comfort may be employed. Such a material, specifically, a soft material such as sponge made of urethane foam is exemplified. In addition, by covering such a soft material with a synthetic leather or the like, it is possible to improve the wearing comfort and design of the spacer 722.

The auxiliary member 73 is formed in a band-like shape as a whole. The auxiliary member 73 is, at one end, connected to the second connection portion 721*b* of the contact member 72. The auxiliary member 73 is, at the other end, connected to the display unit 4. A posture with respect to the display unit 4 is configured to be variable. In this embodiment, the auxiliary member 73 includes a band 731 and an attachment tool 732.

The band 731 includes an end portion to be connected to the second connection portion 721*b* and an end portion to be connected to the attachment tool 732 on the side of the display unit 4. The band 731 is made of, for example, a soft material. Specifically, a deformable material such as cloth made of polypropylene or the like, a resin material made of polyvinyl chloride or the like, and a rubber material may be employed.

The attachment tool 732 is attached to the end portion of the band 731 on the side of the display unit 4. The attachment tool 732 is connected to the attachment holes 412 of the display unit 4. The attachment tool 732 is formed of, for example, a rectangular plate-shape in which a groove to be fitted onto the end portion of the band 731 is formed. A shaft portion 732*a* is formed along the x-axis direction in the attachment tool 732. The shaft portion 732*a* is opposed to the opening of the groove. The shaft portion 732*a* is engaged to be rotatable with respect to the pair of attachment holes 412*a* of the display unit 4. With this, the auxiliary member 73 is connected to be rotatable around the x-axis with respect to the display unit 4. Further, at both ends of the shaft portion 732*a*, which are opposed to each other in the x-axis direction, a pair of stoppers (not shown) or the like may be formed. The pair of stoppers prevent the shaft portion 732*a* from being detached through the attachment holes 412*a* in the x-axis direction.

Note that the configuration of the auxiliary member 73 is not limited to the above-mentioned configuration. For example, a separate attachment tool does not need to be provided and the band and the attachment tool may be integrated with each other.

In addition, in this embodiment, the support mechanism 7 includes the cover member 74 and the spring-supporting member 75.

FIG. 7 is a perspective view showing configurations of main parts of the support mechanism 7. Specifically, FIG. 7 shows configurations of the contact member 72, the cover member 74, and the spring-supporting member 75. Note that, for the sake of description, the contact member 72 is shown in a state in which the right half thereof is cut off.

The cover member 74 is connected to the elastic member 71. The cover member 74 is configured to be engaged to the contact member 72 and movable with respect to the contact member 72. The cover member 74 is formed along the longitudinal direction of the contact member 72 as a whole. The cover member 74 is configured to be capable of covering the spring 711 and part of the upper surface and right and left side surfaces of the sheath member 721 of the contact member 72. By covering the spring 711, the cover member 74 can prevent deterioration of the spring material 713 due to adhesion of liquid, contact of the user, and the like. At the same time, it is possible to prevent an operation failure due to catching of foreign matter by the spring 711 or the like.

In this embodiment, the cover member 74 is connected to be rotatable around the rotation shaft L of the spring 711 via the spring-supporting member 75. The cover member 74 is configured to support the rotation shaft L to be rotatable. Note that, in FIG. 7, illustration of the rotation shaft L is omitted.

The cover member 74 includes engagement portions 741 to be engaged to the contact member 72. The engagement portions 741 are configured to be engageable to the engagement grooves 721*d*. For example, the engagement portions 741 protrude from the left and right side surfaces of the cover member 74 to an inside of the cover member 74 (in x-axis direction). The engagement portions 741 are formed of a pair of protrusions formed along the longitudinal direction.

With the above-mentioned configuration, the contact member 72 is configured to be engaged to the cover member 74 while being slidable. That is, the contact member 72 is movable to be pulled out from the cover member 74 in the y-axis direction or to be pulled into the cover member 74. Thus, the contact member 72 can operate smoothly. With this, also the elastic member 71 to be connected to the contact member 72 can stretch and contract between the first length and the second length.

The spring-supporting member 75 is configured to support the rotation shaft L to be rotatable. In this embodiment, the spring-supporting member 75 includes, for example, the left and right and front and rear side surfaces and a lower surface, and is configured to house the wheel 712 of the spring 711. Note that the cover member 74 according to this embodiment is configured to rotate with respect to the spring-supporting member 75.

In addition, a coupling member attachment hole 761 is formed in a lower surface of the spring-supporting member 75. The coupling member 63 can be fixed into the coupling member attachment hole 761. The spring-supporting member 75 is connected to the coupling member 63 through the coupling member attachment hole 761 with a screw, for example. Note that a separate member such as a backing plate in which a through-hole is formed, through which a screw is passes, for example, may be further provided between the spring-supporting member 75 and the coupling member 63.

Meanwhile, the mounting unit 5 may further include the pad portion 51. The pad portion 51 is provided in the upper surface of the casing 41. The pad portion 51 is configured to be brought into contact with the forehead of the user during mounting. The pad portion 51 is configured to be capable of fixing the mounting position of the display unit 4 in the front and rear directions together with the band member 64.

The pad portion 51 may include a pad main body attached to the casing 41 to be opposed to the user via, for example, a pad attachment mechanism. The configuration of the pad attachment mechanism is not particularly limited. For example, the pad attachment mechanism may include a rotation shaft extending in the x-axis direction such that the pad main body is rotatable around the x-axis with respect to the casing 41. With this, an angle of the pad portion 51 around the x-axis can be changed. Thus, it is possible to adjust the mounting position to be a more comfortable mounting position depending on each user.

Further, the pad portion 51 may be capable of changing the mounting position of the pad main body in the z-axis direction. Also with this, it is possible to adjust the mounting position of the pad portion 51 to a more suitable one.

In addition, the pad portion 51 may be provided with a soft cushion material made of urethane foam or the like on a side of the pad main body to be brought into contact with the user. With this, it is possible to improve the wearing comfort.

By the mounting unit 5 having the above-mentioned configuration, the display unit 4 is supported and mounted in front of the eyes of the user. Next, a mounting method for the HMD 1 will be described.

Mounting Method

First, the user outwardly spreads the left and right connection members 61 and 62 to the left and right, and the HMD 1 is put on the head from above the user. In this embodiment, the connection members 61 and 62 are made of the elastic material, and hence such an operation is possible. At this time, the display unit 4, the connection members 61 and 62, and the like are lowered from the parietal region toward the neck of the user.

At this time, an end portion of the contact member 72 on a side of the auxiliary member 73 is first brought into contact with the vicinity of the parietal region. Then, as the display unit 4 is lowered, the contact member 72 moves forwards, pulled out from the cover member 74. Further, the cover member 74 is attached conforming the shape of a front portion of the parietal region of the user by a rotation around the rotation shaft L. Meanwhile, the coupling member 63 is lowered being fitted onto the temporal regions of the user due to an elastic force of the base material 631.

In this manner, the entire HMD 1 is temporarily mounted on the head of the user. At this time, the connection members 61 and 62 are respectively located on the left and right temporal regions of the user. For example, the connection members 61 and 62 are attached to extend from the vicinities of the left and right temples to the back sides of the auricles. For example, the coupling member 63 is connected to the connection members 61 and 62 above the left and right auricles. The coupling member 63 is attached to extend from the temporal regions to a rear portion of the parietal region. Further, the band member 64 is attached to the occipital region of the user. For example, band member 64 is attached to extend from the back sides of the left and right auricles to the occipital region near the neck. The pad portion 51 is held in contact with the forehead of the user.

Next, the length adjustment mechanism 65 adjusts the length of the coupling member 63 such that the display unit 4 is located at a suitable relative position with respect to the eyes of the user. That is, the length of the coupling member 63 is adjusted such that the display surfaces 42 and the left and right eyes are opposed to each other in the y-axis direction and image light emitted with the y-axis direction being the optical axis direction forms images on the irises of the left and right eyes by an eye-side lens or the like.

Specifically, while viewing images displayed on the display surfaces 42, the user adjusts the position of the display unit 4 and the length of the coupling member 63 such that a desired image is provided. The desired image means, for example, an image in which no focus error occurs or no blur for an 3D image occurs. The image at this time may be an image dedicated for focusing or may be an image captured through the endoscope apparatus 2.

In addition, in the case where the band member 64 includes the length adjustment mechanism and the like, the length adjustment mechanism can be adjusted such that the pad portion 51 lightly presses the forehead of the user at a suitable relative position. With this, the HMD 1 can keep the mounting position also when the head of the user moves in the front and rear directions. Note that, in the case where the band member 64 is made of an elastic material, the mounting position of the HMD 1 can be kept due to an elastic force irrespective of the length adjustment mechanism and the like.

Further, when the mounting position of the HMD 1 is adjusted by the above-mentioned method, the HMD 1 is activated in advance. As the activation method, the pad portion 51 may function as an activation switch and may be activated when pressed by the forehead of the user, for example.

In the process of the above-mentioned mounting method in which the HMD 1 is put on the head, the contact member 72 of the support mechanism 7 is pulled out from the cover member 74 and changes the state thereof. In view of this, operations of the mounting unit 5 when the HMD 1 is put on the head will be next described by focusing on the support mechanism 7.

Operations of Mounting Unit

Figure 8:
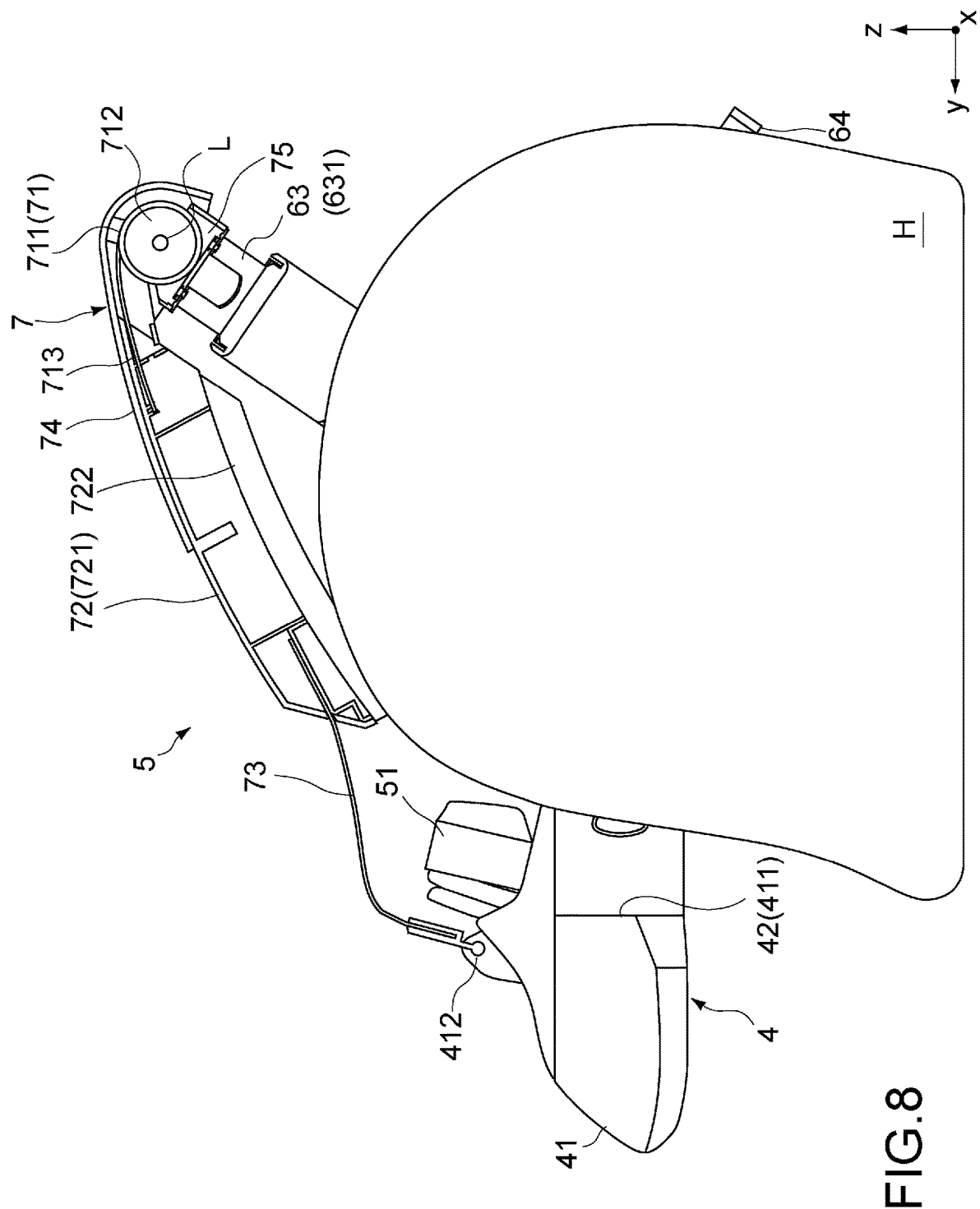
FIG. 8 is a cross-sectional view showing a state directly after a user wears the HMD shown in FIG. 2, as viewed in the x-axis direction.
Figure 9:
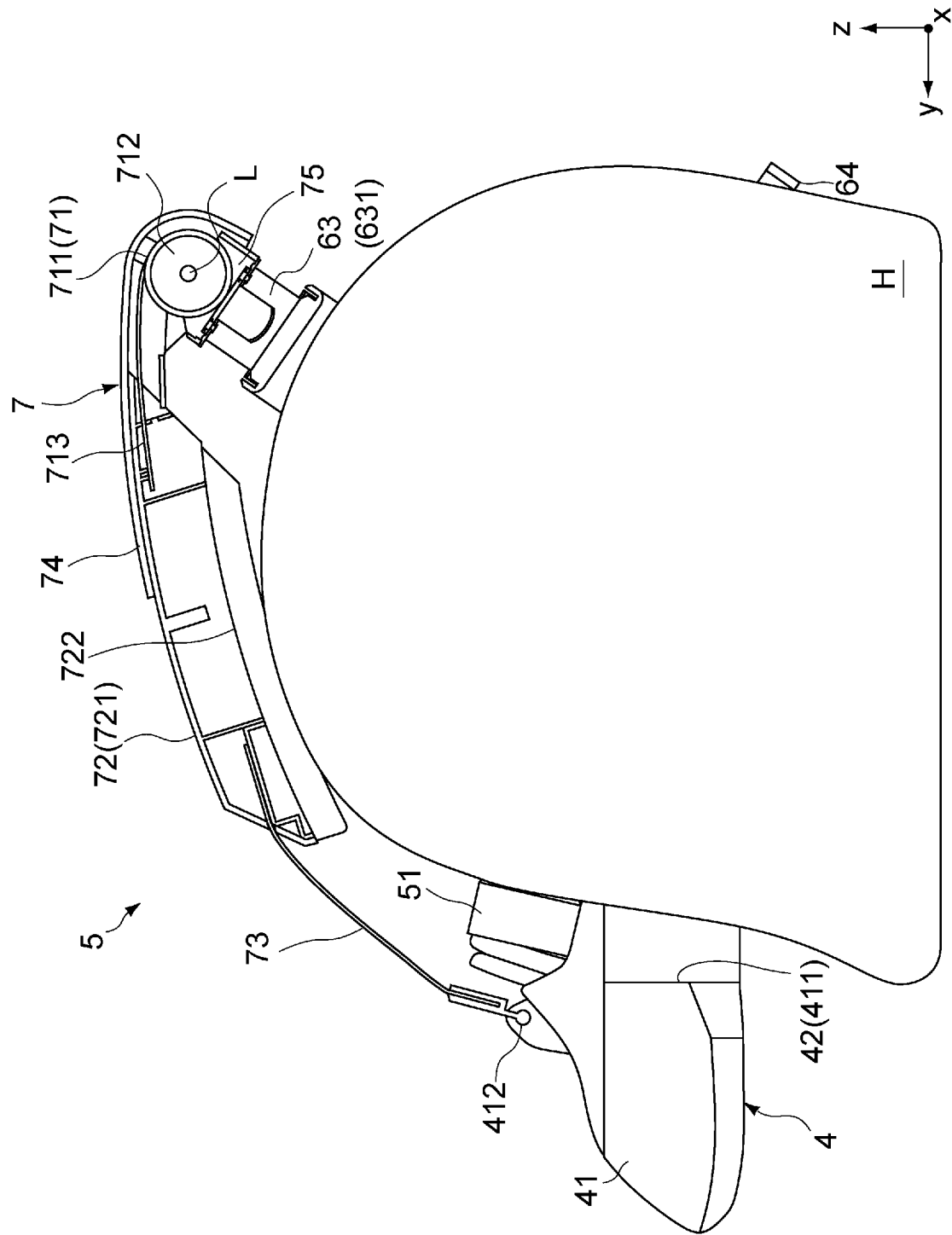
FIG. 9 is a cross-sectional view showing a state in which the HMD is more deeply mounted in comparison with FIG. 8, as viewed in the x-axis direction.
Figure 10:
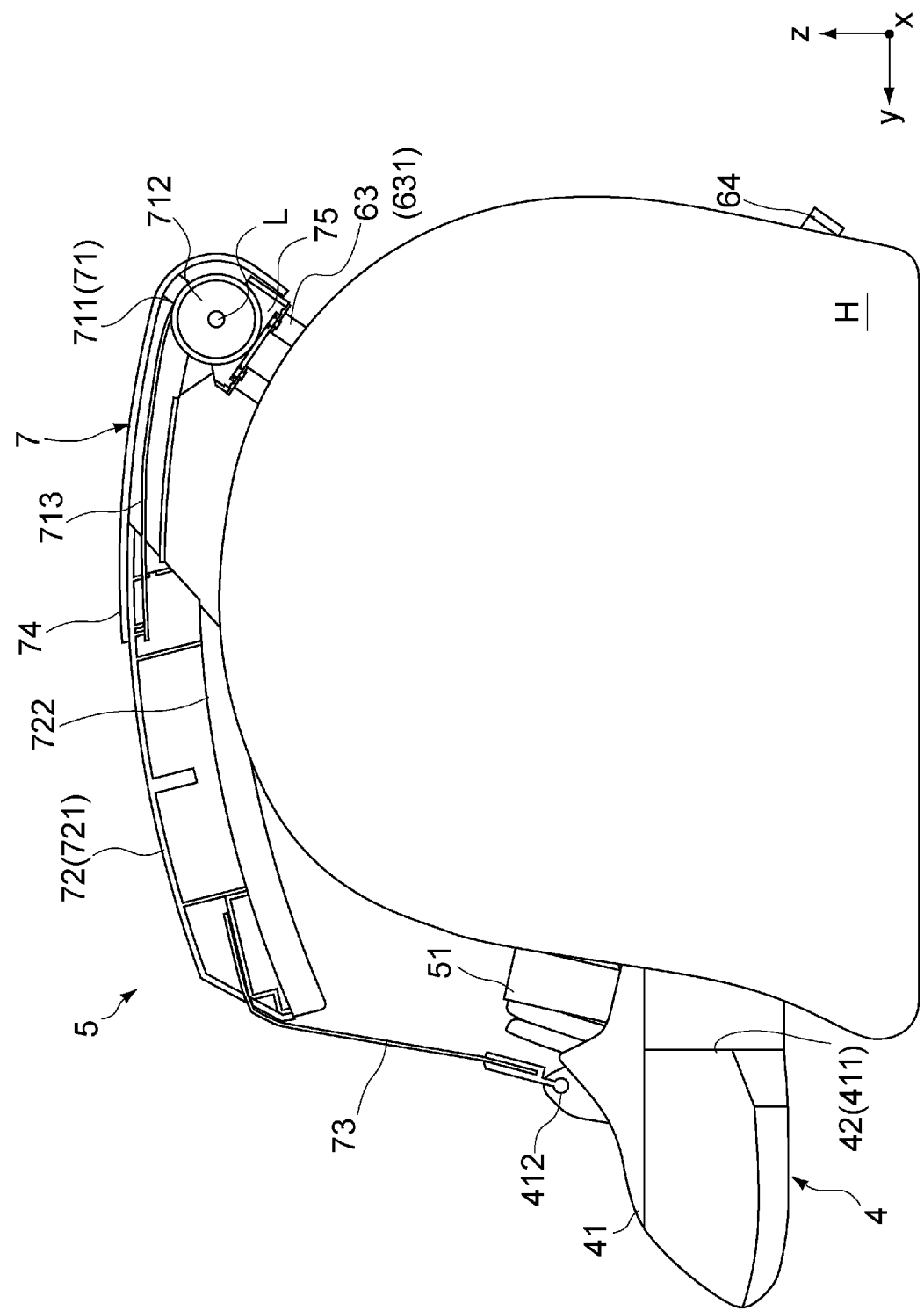
FIG. 10 is a cross-sectional view showing a state in which a display unit of the HMD shown in FIG. 2 is mounted at a suitable relative position, as viewed in the x-axis direction.

FIGS. 8 to 10 are views for explaining operations of the mounting unit 5 when the HMD 1 according to this embodiment is mounted. Specifically, FIGS. 8 to 10 are cross-sectional views as viewed in the x-axis direction. Note that a symbol H in the figures denotes the head of the user.

The HMD 1 during non-mounting is shown in FIG. 3. During non-mounting, the spring 711 has the first length being the natural length. The length by which the contact member 72 and the cover member 74 overlap with each other becomes the maximum. That is, the elastic member 71 does not generate an elastic force. Further, the elastic member 71 (cover member 74) and the contact member 72 are located in a state inclined by, for example, about 30 (with respect to the y-axis direction as viewed in the x-axis direction.

FIG. 8 shows a state of the mounting unit 5 immediately after mounting of the HMD 1 is started. In the contact member 72, the spacer 722 near the end portion on the side of the auxiliary member 73 is held in contact with the head of the user. At this time, as in the non-mounting state, the spring 711 has the first length being the natural length. The length by which the contact member 72 and the cover member 74 overlap with each other is maximum. Further, the cover member 74 and the contact member 72 are inclined as viewed in the x-axis direction as during non-mounting, for example.

Meanwhile, as described above, the coupling member 63 moves downward in the z-axis direction while being fitted onto the temporal regions of the user.

FIG. 9 shows a state in which the HMD 1 is more deeply mounted in comparison with the state shown in FIG. 8. The display unit 4 downwardly moves from the frontal region of the user toward the eyes. At this time, the weight of the display unit 4 and a force are applied to the contact member 72 via the auxiliary member 73. The force is a force to pull down the contact member 72 by the user or the like. With this, the contact member 72 forwardly moves along the head. The position at which the contact member 72 and the head of the user are held in contact with each other moves from the end portion on the side of the display unit 4 toward an end portion on a side of the elastic member 71. Further, in this embodiment, the support mechanism 7 includes the auxiliary member 73, and hence the contact member 72 can smoothly move.

At this time, the contact member 72 is forwardly pulled out from the cover member 74 while being engaged to the engagement portions 741 of the cover member 74. The spring material 713 connected to the contact member 72 is pulled out from the wheel 712 due to forward movement of the contact member 72. With this, the length of the spring 711 becomes the first length or more and the spring 711 generates a slight elastic force.

Meanwhile, the coupling member 63 downwardly moves while being fitted onto the temporal regions of the user near the occipital region. With this movement of the coupling member 63, the cover member 74 rotates around the rotation shaft L conforming the shape of the head. With this, an angle formed by the cover member 74 and the contact member 72 and by the y-axis direction becomes smaller.

Here, the coupling member 63 exerts an elastic force to the temporal regions of the user and receives the counteracting force from the temporal regions of the user. At this time, the counteracting force has a component rearward in the y-axis direction because the rear portions of the temporal regions are inclined. With this, the counteracting force of the elastic force of the spring 711 (elastic member 71) having a component forward in the y-axis direction is overcome by the counteracting force received by the coupling member 63 connected to the elastic member 71. The coupling member 63 is retained on the temporal regions of the user against the elastic force of the elastic member 71. Thus, the coupling member 63 prevents the elastic member 71 and the contact member 72 from sliding forwards. Expansion and generation of an elastic force of the spring 711 are made possible.

FIG. 10 shows a state in which the display unit 4 is mounted at a suitable relative position. For example, the contact member 72 partially protrudes to the front of the head. Further, the contact member 72 and the cover member 74 are arranged to extend from the front portion to the rear portion of the parietal region due to rotation of the cover member 74 around the rotation shaft L. The contact member 72 and the cover member 74 become almost parallel to the y-axis direction, for example. With this, the coupling member 63 is located at the back sides of the temporal regions, for example. In this embodiment, the cover member 74 is rotatable around the rotation shaft L in this manner. The coupling member 63 can be located at a predetermined position irrespective of the shape of the head of the user.

Further, the elastic member 71 is supported by the coupling member 63 and the cover member 74 and located on the back side of the parietal region, for example. With this, the spring material 713 is further pulled out from the wheel 712. The length of the spring 711 becomes the second length.

Here, the support mechanism 7 generates the biasing force having a force component upward in the z-axis direction (vertical upper direction) with respect to the display unit 4 via the contact member 72 and the auxiliary member 73. The elastic member 71 generates an elastic force having a component rearward in the y-axis direction. The elastic force contributes to this biasing force. That is, an elastic force is not generated in the support mechanism 7 during non-mounting as described above. However, during mounting, an elastic force to contribute to the tensile force is generated. The weight of the display unit 4 can be reduced.

Meanwhile, the coupling member 63 receives, from the elastic member 71, the counteracting force of an elastic force having a component forward in the y-axis direction. Here, the coupling member 63 receives, from the head of the user, the counteracting force of its own elastic force having a component rearward in the y-axis direction. With this, the coupling member 63 is fixed at a predetermined position on the back sides of the temporal regions, for example, against an elastic force of the elastic member 71.

In this manner, the support mechanism 7 according to this embodiment can distribute the weight of the display unit 4 via the elastic force of the elastic member 71, as a load to the temporal regions of the user. With this, the load of the display unit 4 does not concentrate to the pad portion 51 and the like, and hence it is possible to reduce the burden on the user. Thus, it is possible to provide the HMD 1 with less burden on the user even if the user wears the display unit 4 for a long time as in an endoscopic surgery.

Further, the contact member 72 receives, from the head of the user, a normal force having a component upward in the z-axis direction. The contact member 72 generates a frictional force rearward in the y-axis direction between the spacer 722 and the head. Thus, the contact member 72 can stretch the spring 711 without moving on the head of the user in the y-axis direction.

In addition, the contact member 72 according to this embodiment includes the spacer 722, and hence the contact member 72 can be brought into contact with the head even if the user has a small head. With this, irrespective of the shape of the head of the user, the spring 711 can be stably stretched. An elastic force can be reliably generated in the elastic member 71.

In addition, the spring 711 according to this embodiment is a constant load spring. If the spring 711 has the second length or more, an elastic force is almost constantly kept. With this, irrespective of the size, the shape, and the like of the head of the user, an elastic force can be made almost constant. An individual difference of the burden on the user or the like can be reduced.

Second Embodiment

Figure 11:
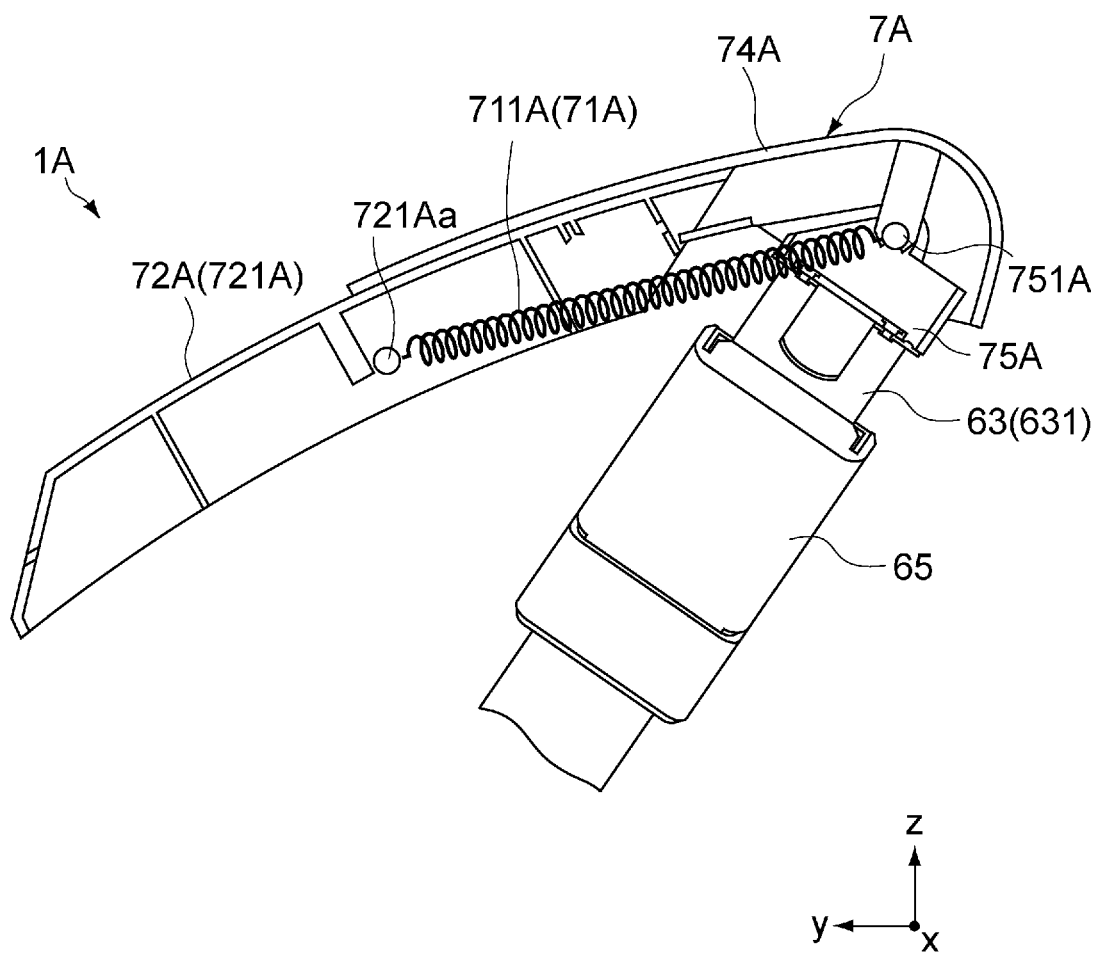
FIG. 11 is a cross-sectional view showing configurations of main-parts of a mounting unit of an HMD according to a second embodiment of the present technology, as viewed in the x-axis direction.

FIG. 11 is a view showing a configuration of the HMD according to a second embodiment of the present technology. Specifically, FIG. 11 is a cross-sectional view of main parts of a mounting unit as viewed in the x-axis direction. Note that, in the figure, portions corresponding to those of the first embodiment described above will be denoted by the same reference symbols and detailed descriptions thereof will be omitted.

An HMD 1A according to this embodiment is different from the first embodiment in that the HMD 1A includes a spring 711A of an elastic member 71A. That is, the spring 711A is formed of an extension coil spring. The spring 711A is, at one end, connected to a first connection portion 721Aa of a contact member 72A. The spring 711A is, at the other end, connected to a connection portion 751A of a spring-supporting member 75A.

The spring 711A is different from a constant load spring. An elastic force is generated according to Hooke's law as follows. That is, provided that F represents a load to a spring, k represents a spring constant, and y represents a displacement, the following equation is established: $F=ky$. With this, a load increases in proportion to a displacement. Also an elastic force as the counteracting force of the load increases in proportion to the displacement.

As in the first embodiment, a sheath member 721A of the contact member 72A includes the first connection portion 721Aa connected to the spring 711A. For example, the first connection portion 721Aa is formed to inwardly protrude from an upper surface of the sheath member 721A. A connection method for the first connection portion 721Aa and an end portion of the spring 711A is not particularly limited. For example, an end portion of the spring 711A may be machined to have a hook-like shape. That hook-like portion may be engaged to a connection hole formed in the first connection portion 721Aa.

Note that, although the illustration is omitted, the contact member 72A may include a spacer as in the first embodiment.

The spring-supporting member 75A includes the connection portion 751A. The spring-supporting member 75A is connected to the coupling member 63 as in the first embodiment. The connection portion 751A is connected to an end portion of the spring 711A on a side of a coupling member 63. For example, the connection portion 751A is formed in a shaft shape protruding in the x-axis direction. A connection method for the first connection portion 721Aa and the spring 711A is not particularly limited. For example, the spring 711A may be connected to the connection portion 751A in such a way that the end portion of the spring 711A is wound around the connection portion 751A.

A cover member 74A is, at one end, supported to be rotatable in the connection portion 751A of the spring-supporting member 75A. The cover member 74A is configured to be capable of covering the spring 711A and the contact member 72A.

With the above-mentioned configuration, the contact member 72A can be pulled out with respect to the cover member 74A as in the first embodiment. With this, it is possible to stretch the spring 711A to generate an elastic force.

As in the first embodiment, also in the above embodiment, the elastic force of the elastic member 71A contributes to the tensile force with respect to a display unit 4. In such a manner that the coupling member 63 connected to the elastic member 71A is mounted on the head of the user, the weight of the display unit 4 can be distributed.

Third Embodiment

Figure 12:
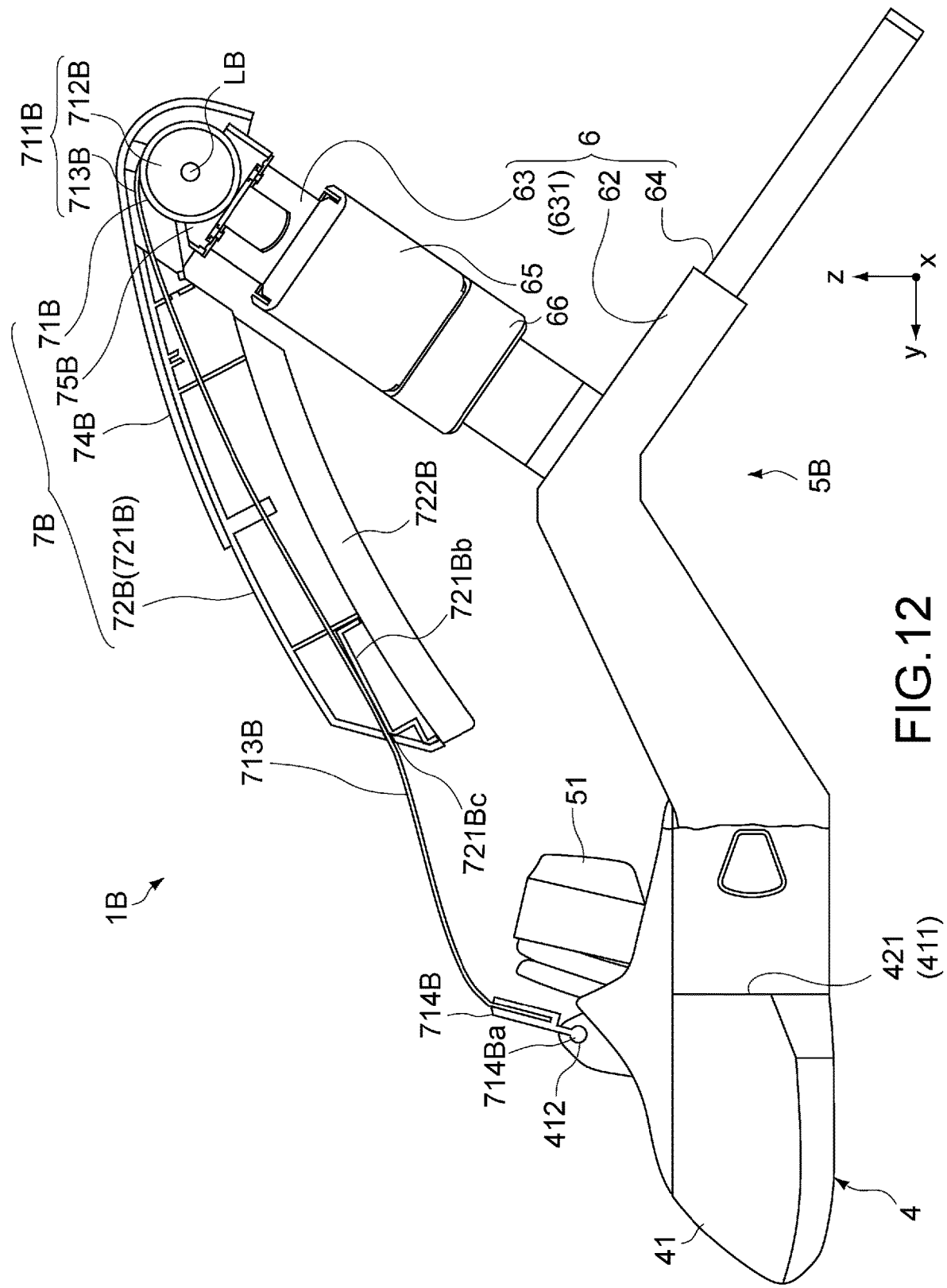
FIG. 12 is a cross-sectional view of an HMD according to a third embodiment of the present technology, as viewed in the x-axis direction.

FIG. 12 is a cross-sectional view of an HMD according to a third embodiment of the present technology, as viewed in the x-axis direction. Note that, in the figure, portions corresponding to those of the first embodiment described above will be denoted by the same reference symbols and detailed descriptions thereof will be omitted.

An HMD 1B according to this embodiment is different from the first embodiment in that the HMD 1B includes a spring 711B of an elastic member 71B. That is, as in the first embodiment, the spring 711B is formed of a constant load spring. However, an end portion of a spring material 713B on a side on which the spring material 713B is pulled out is directly connected to a display unit 4. That is, a support mechanism 7B according to this embodiment does not need to include an auxiliary member.

In this embodiment, for example, an attachment tool 714B is attached to an end portion of the spring material 713B on a side of the display unit 4. The attachment tool 714B may have the same configuration as the attachment tool 732 of the auxiliary member 73 according to the first embodiment. That is, the attachment tool 714B is formed of a rectangular plate shape formed of a groove to be fitted onto an end portion of the spring material 713B. A shaft portion 714B a is formed along the x-axis direction to be opposed to an opening of the groove. Further, the attachment tool 714B is engaged to a pair of attachment holes 412 of the display unit 4 to be rotatable. With this, the end portion of the spring material 713B is connected to the display unit 4 to be rotatable around the x-axis.

A contact member 72B is connected to the elastic member 71B, and mounted on the head of the user such that the elastic member 71B has a length to generate an elastic force during mounting. That is, the contact member 72B is connected also to the display unit 4 via the elastic member 71B. Further, as in the first embodiment, the contact member 72B includes a sheath member 721B and a spacer 722B.

In this embodiment, the sheath member 721B includes a connection portion 721Bb having the same configuration as the second connection portion according to the first embodiment. That is, the connection portion 721Bb may have a seat-like shape including an adhesive surface provided in an inside of the sheath member 721, for example. The connection portion 721Bb is connected to the spring material 713B in such a manner that part of the spring material 713B adheres onto the adhesive surface. Note that the spring material 713B is provided to pass through an insertion hole 721Bc having the same configuration as that of the insertion hole 721c according to the first embodiment.

With the contact member 72B having the above-mentioned configuration, upon mounting of the HMD 1B, the contact member 72B forwardly moves to be pulled out from a cover member 74B while being held in contact with the head of the user as in the first embodiment. In addition, also the contact member 72B according to this embodiment includes the spacer 722B, and hence the contact member 72B can be brought into contact with the head even if the user has a small head. The spring 711B can be stretched. Thus, as in the first embodiment, also the HMD 1B according to this embodiment can cause the elastic member 71B to generate an elastic force irrespective of the size of the head of the user. It is possible to reduce the burden on the user.

Although the embodiments of the present technology will be described, the present technology is not limited thereto and various modifications can be made based on the technical idea of the present technology.

Figure 13:
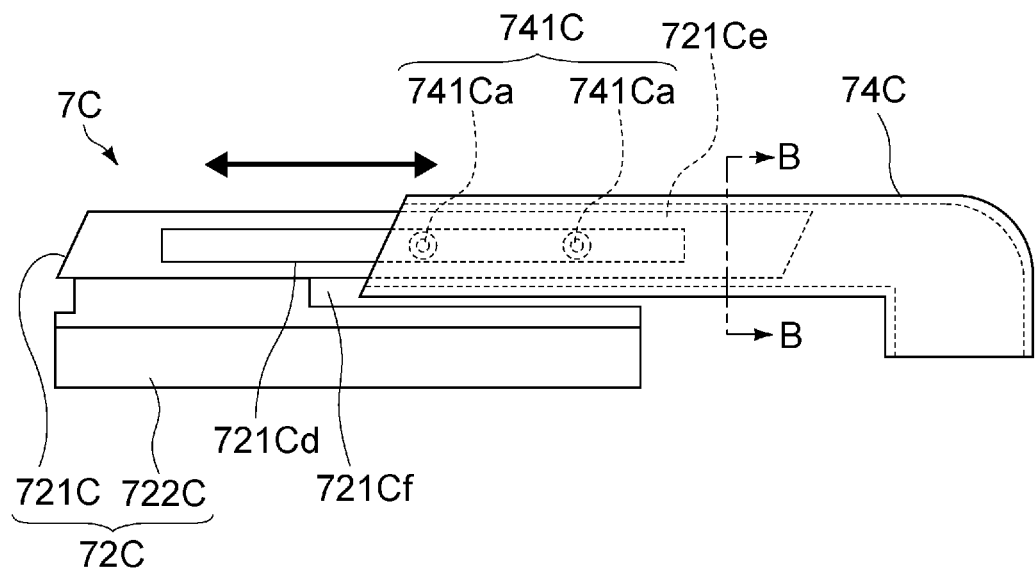
FIG. 13 is a view showing a modified example of the first embodiment of the present technology, more particularly, a schematic side view showing a configuration of a support mechanism.
Figure 14:
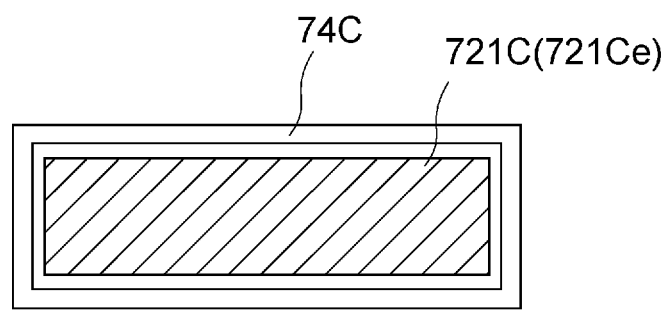
FIG. 14 is a schematic cross-sectional view of the support mechanism shown in FIG. 13, as viewed in the B-B direction of FIG. 13.
Figure 15:
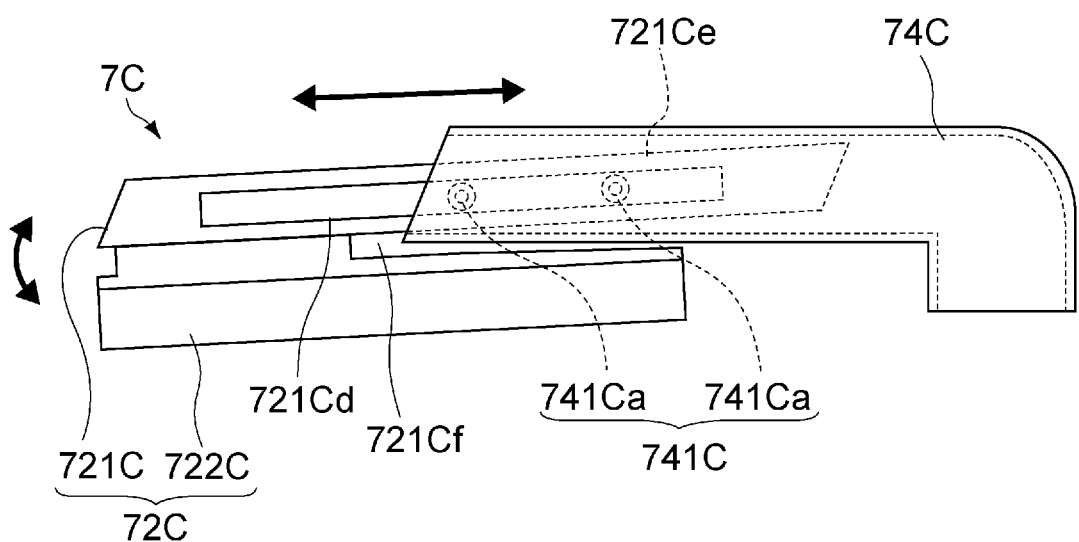
FIG. 15 is a view showing another modified example of the first embodiment of the present technology, more particularly, a schematic side view showing a configuration of a support mechanism.

FIGS. 13 to 15 are views showing modified examples of the first embodiment. FIGS. 13 and 15 are schematic side views showing a relationship between the contact member and the cover member. FIG. 14 is a cross-sectional view as viewed in the B-B direction of FIG. 13. In those modified examples, a configuration of an engagement portion 741C of a cover member 74C is different. That is, the engagement portion 741C includes not protrusions formed along the longitudinal direction, but rollers to be engaged to an engagement groove 721Cd of a contact member 72C.

The engagement portion 741C of FIG. 13 includes two pairs of rollers 741Ca. In this modified example, the pair of rollers 741Ca of the two pairs of rollers 741Ca are arranged in left and right inner side surfaces of the cover member 74C to be opposed to each other in the x-axis direction. For example, shafts of those rollers 741Ca are provided to protrude from the left and right inner side surfaces of the cover member 74C inwardly in the x-axis direction. The two pairs of rollers 741Ca having such a configuration are arranged along a longitudinal direction of the cover member 74C.

Also in this modified example, the contact member 72C can move along the longitudinal direction of the cover member 74C, that is, a direction linking between the two pairs of rollers 741Ca. In addition, the two pairs of rollers 741Ca can make operations of the cover member 74C and the contact member 72C smoother.

Further, as shown in FIG. 14, in this configuration example, a sheath member 721C may include a stick-like portion 721Ce and a groove portion 721Cf. The stick-like portion 721Ce protrudes rearward along the longitudinal direction of the sheath member 721C. The groove portion 721Cf is formed along the longitudinal direction and located between the stick-like portion 721Ce and a spacer 722C. With this, the cover member 74C is configured to cover upper and lower surfaces and left and right side surfaces of the stick-like portion 721Ce. Thus, the contact member 72C can more stably operate with respect to the cover member 74C.

The engagement portion 741C of FIG. 15 includes a pair of rollers 741Ca. The pair of rollers 741Ca are also arranged in left and right side surfaces of the engagement portion 741C to be opposed to each other in the x-axis direction.

According to this modified example, the contact member 72C can move along the longitudinal direction of the cover member 74C. In addition, the contact member 72C can rotate around the x-axis about the pair of rollers 741Ca. With this, for example, even if the cover member 74C cannot rotate around a center of the elastic member, the contact member 72C is attached conforming the head of the user.

Thus, the coupling member 63 can be attached at a predetermined position, for example, the back of the temporal regions.

Further, also in this modified example, as shown in FIG. 14, the sheath member 721C may include the stick-like portion 721Ce and the groove portion 721Cf. The cover member 74C may be configured to cover the upper and lower surfaces and the left and right side surfaces of the stick-like portion 721Ce. In this case, in order to prevent the rotation of the sheath member 721C, an inner surface of the cover member 74C only needs to be configured to be sufficiently large in comparison with a peripheral surface of the stick-like portion 721Ce.

Note that the engagement portion 741C according to the above-mentioned modified example can be realized even replacing a non-rotating shaft member (boss) by the roller.

Further, although the elastic member is the constant load spring or the extension coil spring in the above embodiments, the elastic member is not limited thereto. For example, another spring such as a torsion coil spring and a compression coil spring or another elastic material such as a rubber material may be employed.

In addition, the support mechanism is not limited to the configuration having the elastic member. A configuration capable of generating the biasing force to contribute as the tensile force with respect to the display unit during mounting only needs to be employed. For example, the support mechanism may include a winch including a driving source such as a motor and winds up a wire rope or the like connected to the display unit. With this, during mounting, the driving source generates a biasing force to wind up the wire rope or the like. That biasing force contributes to the tensile force, such that the display unit can be lifted up. Further, the display unit can be supported with a constant force irrespective of the shape of the head of the user.

Although a configuration in which the HMD includes the single support mechanism is employed in the above embodiments, the configuration is not limited thereto. For example, the HMD may include two or more support mechanisms and those support mechanisms may be connected to the display unit 4 in parallel. With this, a larger elastic force can be generated.

Further, a configuration in which the support mechanism includes a plurality of elastic members (springs or the like) may be employed. For example, the support mechanism may have a configuration in which a plurality of springs are connected in series or a configuration in which a plurality of springs are connected in parallel.

Although a configuration in which the mounting unit and the coupling member are arranged on the temporal regions is employed in the above embodiments, the present technology is not limited thereto. For example, the coupling member may be mounted from the elastic member on the parietal region to the occipital region and may be provided to extend from the support mechanism. In this case, the coupling member can fix the mounting position in the front and rear directions and a configuration without the band member can be provided.

In addition, the order for connecting the elements of the support mechanism is not limited to the above-mentioned order. For example, the elastic member and the contact member may be connected in the stated order from the side of the display unit. Alternatively, the auxiliary member, a first contact member, the elastic member, a second contact member may be connected in the stated order from the side of the display unit. In this manner, a configuration without the auxiliary member may be employed. A configuration including a plurality of contact members may be employed.

It should be noted that the present technology may also be configured as follows.

(1) A mounting apparatus for dispersing a weight of a device, the mounting apparatus comprising:
a main body configured to support the device and configured to mount on a head of a user; and
a support mechanism, connected to the device and the main body, comprising an elastic member configured to:
have a first length when the mounting apparatus is not mounted on the head of the user such that a first biasing force is applied; and
have a second length larger than the first length when the mounting apparatus is mounted on the head of the user such that the weight of the device is dispersed by applying a second biasing force, which is greater than the first biasing force, with a force component in the vertical direction to the device.

(2) The mounting apparatus according to (1), wherein a biasing force applied by the elastic member is substantially nonlinearly related to the length of the elastic member.

(3) The mounting apparatus according to (1), wherein the elastic member is a constant load spring.

(4) The mounting apparatus according to (1), wherein the elastic member has a first spring constant for a first range of lengths and a second spring constant for a second range of lengths.

(5) The mounting apparatus according to (4), wherein:
the lengths of the first range of lengths are smaller than the lengths of the second range of lengths; and
the first spring constant is greater than the second spring constant.

(6) The mounting apparatus according to (1), wherein the second biasing force applied by the elastic member when the elastic member is a second length is substantially equal to a third biasing force applied by the elastic member when the elastic member is a third length larger than the second length.

(7) The mounting apparatus according to (1), further comprising:
a contact member configured to contact the head of the user when the mounting apparatus is mounted on the head of the user.

(8) The mounting apparatus according to (7), wherein:
the elastic member has a first spring constant for a first range of lengths;
the elastic member has a second spring constant larger than the first spring constant for a second range of lengths comprising lengths that are larger than lengths of the first range of lengths; and
when the mounting apparatus is mounted on the head of the user with the contact member in contact with the head of the user, the elastic member is a length that is within the second range of lengths.

(9) The mounting apparatus according to (8), wherein a sized of the contact member is selected such that, if the contact member was not present, the elastic member would be a length within the first range of lengths when the mounting apparatus is mounted on the head of the user.

(10) The mounting apparatus according to (7), wherein the contact member creates a frictional force with a force component in the vertical direction to the device.

(11) The mounting apparatus according to (7), wherein the contact member comprises a spacer configured to be in contact with the head of the user.

(12) The mounting apparatus according to (11), wherein the spacer comprises a urethane foam material

(13) The mounting apparatus according to (7), wherein the contact member is moveable with respect to the elastic member.

(14) The mounting apparatus according to (1), wherein the device is a display device.

(15) The mounting apparatus according to (14), wherein the display device is configured to display medical images.

(16) The mounting apparatus according to (15), wherein the medical images are images captured by an endoscope.

(17) The mounting apparatus according to (14), wherein the display device is configured to display a first image for the left eye of the user and a second image for the right eye of the user.

(18) The mounting apparatus according to (17), wherein the first and second image are configured such that the user perceives a three-dimensional image.

(19) The mounting apparatus according to (1), wherein the support mechanism is configured to be located on top of the head of the user when the mounting apparatus is mounted on the head of the user.

(20) An endoscopic system, comprising:
an endoscope comprising at least one image sensor for obtaining images; and
a head-mounted display, comprising:
a display device for displaying the images from the endoscope;
a main body configured to support the display device and configured to mount on a head of a user; and
a support mechanism, connected to the device and the main body, comprising an elastic member configured to:
have a first length when the mounting apparatus is not mounted on the head of the user such that a first biasing force is applied; and
have a second length larger than the first length when mounted on the head of the user such that the weight of the device is dispersed by applying a second biasing force, which is greater than the first biasing force, with a force component in the vertical direction to the device.

(21) A head-mounted display, comprising:
a display unit cable of displaying an image in front of an eye of a user; and
a mounting unit including
a main body that is configured to support the display unit and mounted on a head of the user, and
a support mechanism that is connected between the display unit and the main body and capable of generating a biasing force to contribute as a tensile force with respect to the display unit during mounting.

(22) The head-mounted display according to Item (21), in which the support mechanism is configured to generate a biasing force having a force component, the component being oriented in a vertical upper direction.

(23) The head-mounted display according to Item (21) or (22), in which the support mechanism includes an elastic member configured to have a first length during non-mounting, have a second length larger than the first length during mounting, and generate an elastic force as the biasing force.

(24) The head-mounted display according to Item (23), in which the elastic member includes a spring configured to generate a constant elastic force with the second length and with a third length larger than the second length.

(25) The head-mounted display according to Item (23) or (24), in which the support mechanism further includes a contact member that is connected to the display unit and the elastic member and mounted on the head of the user such that the elastic member has the second length during mounting.

(26) The head-mounted display according to Item (25), in which the support mechanism further includes an auxiliary member that is connected to the display unit and the contact member and configured to be capable of changing a posture thereof with respect to the display unit.

(27) The head-mounted display according to Item (26), in which the auxiliary member is connected to the display unit to be rotatable.

(28) The head-mounted display according to Item (26) or (27), in which the auxiliary member is formed of a soft material.

(29) The head-mounted display according to any one of Items (25) to (28), in which the support mechanism further includes a cover member configured to be engaged to the contact member and cover the elastic member, and
the contact member is configured to be engaged to the cover member while being slidable to cause the elastic member to stretch and contract between the first length and the second length.

(30) The head-mounted display according to any one of Items (21) to (29), in which the display unit includes a display surface capable of emitting image light in a first axis direction,
the main body includes
two connection members that are connected to the display unit and opposed to each other in a second axis direction orthogonal to the first axis direction,
a coupling member configured to couple between the two connection members in an arch shape, and
a band member that is connected between the two connection members and opposed to the display unit in the first axis direction, and
the support mechanism is connected to the coupling member.

The present application contains subject matter related to that disclosed in Japanese Priority Patent Application JP 2012-212087 filed in the Japan Patent Office on Sep. 26, 2012, the entire content of which is hereby incorporated by reference.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST 1, 1A, 1B Head-mounted display (HMD)
4 Display unit
5, 5A, 5B Mounting unit
6 Main body
7, 7A, 7B Support mechanism
42 Display surface
61, 62 Connection member
63 Coupling member
64 Band member
71, 71A, 71B Elastic member
72, 72A, 72B Contact member
74, 74A, 74B Cover member
711, 711A, 711B Spring

The invention claimed is:
1. A mounting apparatus comprising:
a device including a display configured to display an image to a user, a goggle-shaped, non-see-through housing, and a display circuit configured to generate the image and to output the image to the display; and
a mounting portion including:
two connection portions, each connection portion having a front end and a rear end and being coupled to the housing of the device at the front end,
a first coupling portion that is coupled to the rear ends of the two connection portions and extends from the rear ends of the two connection portions in a first direction, and has an arch shape,
a second coupling portion that is coupled to the rear ends of the two connection portions and that extends under the arch shape in a second direction different from the first direction; and
a head support member, connected between the housing of the device and a top of the arch shape, configured to:
have a first length when the mounting apparatus is not mounted on a head of the user; and
have a second length larger than the first length when the mounting apparatus is mounted on the head of the user such that the weight of the device is dispersed, wherein the top of the arch shape of the first coupling portion is located at a rear portion of a top of the head of the user when the mounting apparatus is mounted on the head of the user, wherein the first coupling portion and the second coupling portion support the rear portion of the top of the head of the user without use of a chin strap and wherein the head support member is connected directly between the housing and the top of the arch shape of the first coupling portion at the rear portion of the top of the head of the user, and extends in a front-to-back direction between the housing and the first coupling portion.

2. The mounting apparatus according to claim 1, wherein the head support member includes an elastic member and wherein a biasing force applied by the elastic member is nonlinearly related to a length of the elastic member.

3. The mounting apparatus according to claim 1, wherein the head support member includes an elastic member and wherein the elastic member is a constant load spring.

4. The mounting apparatus according to claim 1, wherein the head support member includes an elastic member and wherein the elastic member has a first spring constant for a first range of lengths and a second spring constant for a second range of lengths.

5. The mounting apparatus according to claim 4, wherein:
the lengths of the first range of lengths are smaller than the lengths of the second range of lengths; and
the first spring constant is greater than the second spring constant.

6. The mounting apparatus according to claim 1, wherein the head support member includes an elastic member that applies a first biasing force when the mounting apparatus is not mounted on the head of the user and applies a second biasing force, greater than the first biasing force, when the mounting apparatus is mounted on the head of the user and wherein the second biasing force applied by the elastic member when the elastic member is the second length is equal to a third biasing force applied by the elastic member when the elastic member is a third length larger than the second length.

7. The mounting apparatus according to claim 1, wherein the head support member includes an elastic member and a contact member and wherein the contact member is configured to contact the head of the user when the mounting apparatus is mounted on the head of the user.

8. The mounting apparatus according to claim 7, wherein:
the elastic member has a first spring constant for a first range of lengths;
the elastic member has a second spring constant larger than the first spring constant for a second range of lengths comprising lengths that are larger than lengths of the first range of lengths; and
when the mounting apparatus is mounted on the head of the user with the contact member in contact with the head of the user, the elastic member is a length that is within the second range of lengths.

9. The mounting apparatus according to claim 8, wherein a size of the contact member is selected such that, if the contact member was not present, the elastic member would be a length within the first range of lengths when the mounting apparatus is mounted on the head of the user.

10. The mounting apparatus according to claim 7, wherein the contact member creates a frictional force with a force component in a vertical direction to the device.

11. The mounting apparatus according to claim 7, wherein the contact member comprises a spacer configured to be in contact with the head of the user.

12. The mounting apparatus according to claim 11, wherein the spacer comprises a urethane foam material.

13. The mounting apparatus according to claim 7, wherein the contact member is moveable with respect to the elastic member.

14. The mounting apparatus according to claim 1, wherein the device is configured to display medical images.

15. The mounting apparatus according to claim 14, wherein the medical images are images captured by an endoscope.

16. The mounting apparatus according to claim 1, wherein the device is configured to display a first image for the left eye of the user and a second image for the right eye of the user.

17. The mounting apparatus according to claim 1, wherein the head support member is configured to be located on top of the head of the user when the mounting apparatus is mounted on the head of the user.

18. The mounting apparatus according to claim 1, wherein the first coupling portion is coupled to each of the two connection portions at a first angle.

19. The mounting apparatus according to claim 18, wherein the second coupling portion is coupled to each of the connection portions at a second angle opposite to the first angle.

20. The mounting apparatus according to claim 18, wherein the two connection portions are partially bent.

21. An endoscopic system, comprising:
an endoscope comprising at least one image sensor for obtaining images; and
a head-mounted display, comprising:
a display device for displaying the images from the endoscope;
a mounting portion including:
two connection portions, each connection portion having a front end and a rear end and being coupled to the device at the front end,
a first coupling portion that is coupled to the rear ends of the two connection portions and extends from the rear ends of the two connection portions in a first direction, and has an arch shape,
a second coupling portion that is coupled to the rear ends of the two connection portions and that extends under the arch shape in a second direction different from the first direction; and a head support member, connected between the device and a top of the arch shape, configured to:
have a first length when the mounting portion is not mounted on a head of a user; and
have a second length larger than the first length when mounted on the head of the user such that a weight of the device is dispersed, wherein the top of the arch shape of the first coupling portion is located at a rear portion of a top of the head of the user when the mounting portion is mounted on the head of the user, wherein the first coupling portion and the second coupling portion support the rear portion of the top of the head of the user without use of a chin strap and wherein the head support member is connected directly between the housing and the top of the arch shape of the first coupling portion at the rear portion of the top of the head of the user, and extends in a front-to-back direction between the housing and the first coupling portion.

22. A head mounted display comprising:
a device configured to display an image to a user; and
a mounting portion including:
two connection portions, each having a front end and a rear end and being coupled to the device at the front end,
a first coupling portion that is coupled to the rear ends of the two connection portions and extends from the rear ends of the two connection portions in a first direction, and has an arch shape,
a second coupling portion that is coupled to the rear ends of the two connection portions and that extends under the arch shape in a second direction different from the first direction; and
a head support member that is coupled between the device and a top of the arch shape and has a length adjustment mechanism, wherein the top of the arch shape of the first coupling portion is located at a rear portion of a top of the head of the user when the mounting portion is mounted on the head of the user, wherein the first coupling portion and the second coupling portion support the rear portion of the top of the head of the user without use of a chin strap and wherein the head support member is connected directly between the housing and the top of the arch shape of the first coupling portion at the rear portion of the top of the head of the user, and extends in a front-to-back direction between the housing and the first coupling portion.

* * * * *